(12) United States Patent
Brodin et al.

(10) Patent No.: US 7,425,623 B2
(45) Date of Patent: Sep. 16, 2008

(54) ANTIBODY WITH SPECIFICITY FOR COLON CANCER

(75) Inventors: Thomas N. Brodin, Råå (SE); Pia J. Karlström, Lund (SE); Lennart G Ohlsson, Lund (SE); Jesper M Tordsson, Lund (SE); Bo H K. Nilson, Lund (SE)

(73) Assignee: Active Biotech AB, Lund (SE)

( * ) Notice: Subject to any disclaimer, the term of this patent is extended or adjusted under 35 U.S.C. 154(b) by 991 days.

(21) Appl. No.: 10/182,132

(22) PCT Filed: Feb. 23, 2001

(86) PCT No.: PCT/SE01/00395

§ 371 (c)(1),
(2), (4) Date: Sep. 5, 2002

(87) PCT Pub. No.: WO01/62286

PCT Pub. Date: Aug. 30, 2001

(65) Prior Publication Data

US 2003/0176661 A1    Sep. 18, 2003

(30) Foreign Application Priority Data

Feb. 24, 2000   (SE)   .................... 0000597

(51) Int. Cl.
C07K 16/30 (2006.01)
C07K 16/18 (2006.01)
A61K 47/42 (2006.01)
G01N 33/68 (2006.01)
C07H 21/04 (2006.01)

(52) U.S. Cl. .................. 530/388.8; 424/144.1

(58) Field of Classification Search .............. 530/387.1, 530/388.7, 388.8; 424/130.1, 153.1, 133.1, 424/135.1, 144.1
See application file for complete search history.

(56) References Cited

U.S. PATENT DOCUMENTS 5,843,686 A * 12/1998 Zain et al. .................. 435/7.23

OTHER PUBLICATIONS

Tockman et al. (Cancer Res., 1992, 52:2711s-2718s).*
Slamon et al. (Science vol. 235, Jan. 1987, pp. 177-182).*
Rudikoff et al (Proc. Natl. Acad. Sci. USA 1982 vol. 79 p. 1979).*
Burgess et al, Journal of Cell Biology vol. 111 Nov. 1990 2129-2138.*
Lazar et al Molecular and Cellular Biology Mar. 1988 vol. 8 No. 3 1247-1252).*
Lin et al Biochemistry USA vol. 14:1559-1563 (1975).*
Acland et al., Nature vol. 343:662-665 (1990).*
Ibragimova and Eade (Biophysical Journal, Oct. 1999, vol. 77, pp. 2191-2198).*
Burgess et al. Journal of Cell Biology, 111. 1990, 2129-2138.*
Lazar et al. Molecular and Cellular Biology Mar. 1988 vol. 8 No. 3 1247-1252.*
Rudikoff et al. Proc. Natl. Acad. Sci. USA 1982 vol. 79 p. 1979, 1983.*
Colman et al. Research in Immunology 1994, 145:33-36.*
Ibragimova and Eade. Biophysical Journal, Oct. 1999, vol. 77, pp. 2191-2198.*
Epner et al., "Glyceraldehyde-3-Phospate Dehydrogenase Expression During Apoptosis and Proliferation of Rat Ventral Prostate", Biology of Reproduction, 61, 687-691 (1999).
Ishitani et al., "Nuclear Localization of Overexpressed Glyceraldehyde-3-Phophate Dehydrogenase in Cultured Cerebellar Neurons Undergoing Apoptosis", Molecular Biology, 53, 701-707 (1998).
Cuezva et al., "The Bioenergetic Signature of Cancer: A Marker of Tumor Progression", Cancer Research, 62, 6674-6681, Nov. 15, 2002.

* cited by examiner

*Primary Examiner*—Larry R. Helms
*Assistant Examiner*—Lynn Bristol
(74) *Attorney, Agent, or Firm*—Buchanan Ingersoll & Rooney PC

(57) ABSTRACT

A binding structure which binds in, and/or to the surface of, tumour cells; a target structure displayed and/or expressed in, or on the surface of, tumour cells; a binding structure that recognises and blocks said target structure; a substance that binds to or blocks the expression of said target structure; pharmaceutical compositions comprising said binding structure, target structures or substance as active principles; vaccine compositions comprising said target structures as active principles; a method for phage selection; and methods of in vitro and in vivo diagnosis and prognosis, and of treatment of human malignant diseases comprising the use of the above subject matters, are described.

13 Claims, 14 Drawing Sheets

Figure 2:
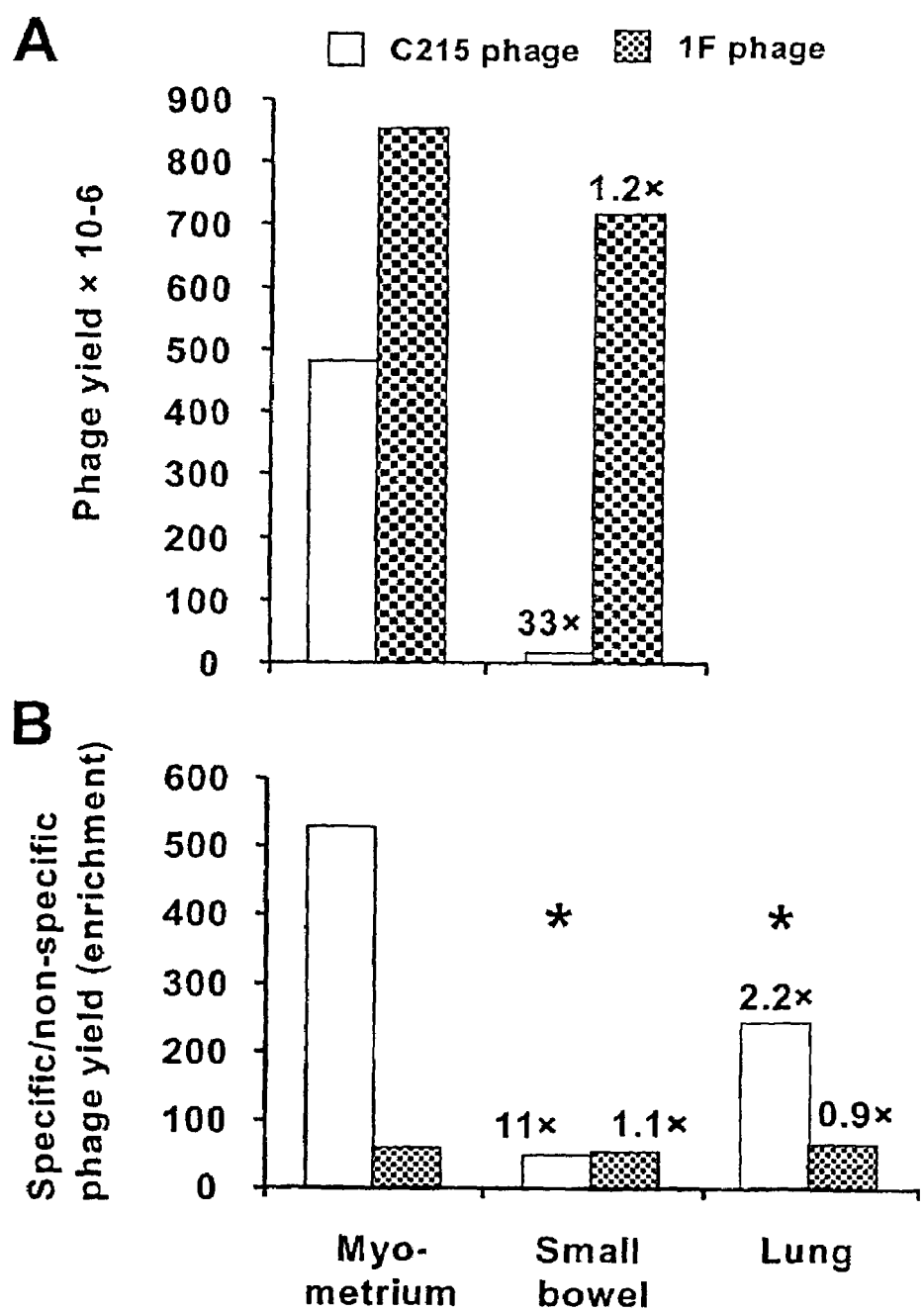

Figure 1
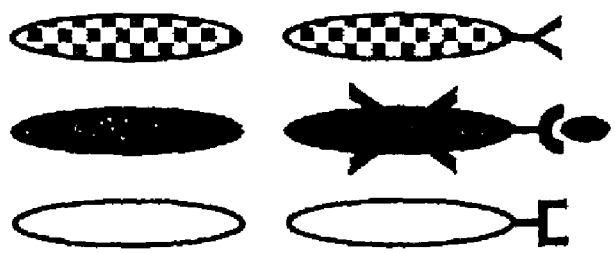
Negative selection
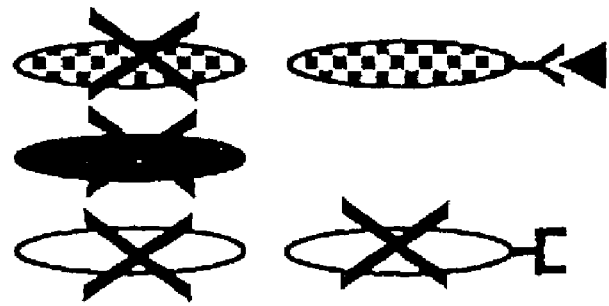
Positive selection
Subtracted phage pool

SEQ ID NO: 3    GALQNIIPAS
SEQ ID NO: 4    VIISAPSADA
SEQ ID NO: 5    VPTANVSVVD

Figure 12. The N-terminal sequences of three tryptic peptide fragments from the 35-45 kDa protein band (labelled A) isolated from K293-affinity purification (see figure 11).

```
1    MGKVKVGVNGFGRIGRLVTRAAFNSGKVDIVAINDPFIDLNYMVYMFQYD

51   STHGKFHGTVKAENGKLVINGNPITIFQERDPSKIKWGDAGAEYVVESTG

101  VFTTMEKAGAHLQGGAKRVIISAPSADAPMFVMGVNHEKYDNSLKIISNA
                        VIISAPSADA

151  SCTTNCLAPLAKVIHDNFGIVEGLMTTVHAITATQKTVDGPSGKLWRDGR

201  GALQNIIPASTGAAKAVGKVIPELNGKLTGMAFRVPTANVSVVDLTCRLE
     GALQNIIPAS                        VPTANVSVVD

251  KPAKYDDIKKVVKQASEGPLKGILGYTEHQVVSSDFNSDTHSSTFDAGAG

301  IALNDHFVKLISWYDNEFGYSNRVVDLMAHMASKE
```

Figure 13. The peptide sequences of SEQ ID NO: 3 to 5 (defined in Figure 12) were aligned with the protein sequence of glyceraldehyde 3-phosphate dehydrogenase (accession no. P04406).

SEQUENCE LISTING

```
<160> NUMBER OF SEQ ID NOS: 2

<210> SEQ ID NO 1
<211> LENGTH: 747
<212> TYPE: DNA
<213> ORGANISM: Macaca fascicularis
<220> FEATURE:
<221> NAME/KEY: CDS
<222> LOCATION: (1)..(747)
<223> OTHER INFORMATION: K293 variable region (scFv); PRT (aa)-sequence
      Vl (1-110), mod Huston (111-129), Vh (130-249)

<400> SEQUENCE: 1 cac gtt ata ttg act cag tcg ccc tct gtg tct ggc tct cct gga cag      48
His Val Ile Leu Thr Gln Ser Pro Ser Val Ser Gly Ser Pro Gly Gln
  1               5                  10                  15 tcg gtc acc ctc tcc tgc act gga acc agc aat gac atc ggt ggc tat      96
Ser Val Thr Leu Ser Cys Thr Gly Thr Ser Asn Asp Ile Gly Gly Tyr
             20                  25                  30 gat tat gtc tcg tgg tat cag cat cac cca ggc aaa gcc ccc aag ctc     144
Asp Tyr Val Ser Trp Tyr Gln His His Pro Gly Lys Ala Pro Lys Leu
         35                  40                  45
```

-continued

```
atg att tac aat gtc aat aag cgg ccc tca ggg gtc tct gag cgc ttc      192
Met Ile Tyr Asn Val Asn Lys Arg Pro Ser Gly Val Ser Glu Arg Phe
     50                  55                  60 tct ggc tcc aag tct gcc aac acg gcc tcc ctg acc atc tct gga ctc      240
Ser Gly Ser Lys Ser Ala Asn Thr Ala Ser Leu Thr Ile Ser Gly Leu
 65                  70                  75                  80 cag gat gac gat gag gct gat tac tat tgc agt tcc tat gca cgc cgg      288
Gln Asp Asp Asp Glu Ala Asp Tyr Tyr Cys Ser Ser Tyr Ala Arg Arg
                 85                  90                  95 gac act tac att ttc ggt ggt ggg acc cgg ctc acc gtc cta ggt caa      336
Asp Thr Tyr Ile Phe Gly Gly Gly Thr Arg Leu Thr Val Leu Gly Gln
             100                 105                 110 gcc aac ggt gaa ggc ggc tct ggt ggc ggg gga tcc gga ggc ggc ggt      384
Ala Asn Gly Glu Gly Gly Ser Gly Gly Gly Gly Ser Gly Gly Gly Gly
         115                 120                 125 tct gag gtg cag ctg cag gag tgg ggc cca gga ctg gtg aag cct tcg      432
Ser Glu Val Gln Leu Gln Glu Trp Gly Pro Gly Leu Val Lys Pro Ser
    130                 135                 140 gag acc ctg tcc ctc acc tgc gct gtc tct ggt ttc tcc atc agc agt      480
Glu Thr Leu Ser Leu Thr Cys Ala Val Ser Gly Phe Ser Ile Ser Ser
145                 150                 155                 160 ggt tat ggc tgg agc tgg atc cgt cag tcc cca ggg aag gga ctg gaa      528
Gly Tyr Gly Trp Ser Trp Ile Arg Gln Ser Pro Gly Lys Gly Leu Glu
                165                 170                 175 tgg att gga gac atc tct tat agt ggg aac tcc agg tac aac ccg tcc      576
Trp Ile Gly Asp Ile Ser Tyr Ser Gly Asn Ser Arg Tyr Asn Pro Ser
            180                 185                 190 ctc aag agt cga gtc acc att tca aga gac acg tcc aag aac cag ttc      624
Leu Lys Ser Arg Val Thr Ile Ser Arg Asp Thr Ser Lys Asn Gln Phe
        195                 200                 205 tcc ctg aag ctg acc tct gtg acc gcc gcg gac acg gcc gtg tat tac      672
Ser Leu Lys Leu Thr Ser Val Thr Ala Ala Asp Thr Ala Val Tyr Tyr
    210                 215                 220 tgt gcg aga cat gat aga ggc tgg cac gaa tac ttc gac ttc tgg ggc      720
Cys Ala Arg His Asp Arg Gly Trp His Glu Tyr Phe Asp Phe Trp Gly
225                 230                 235                 240 cag gga gtc ctg gtc acc gtt tcc tca                                  747
Gln Gly Val Leu Val Thr Val Ser Ser
                245

<210> SEQ ID NO 2
<211> LENGTH: 249
<212> TYPE: PRT
<213> ORGANISM: Macaca fascicularis

<400> SEQUENCE: 2

His Val Ile Leu Thr Gln Ser Pro Ser Val Ser Gly Ser Pro Gly Gln
 1               5                   10                  15

Ser Val Thr Leu Ser Cys Thr Gly Thr Ser Asn Asp Ile Gly Gly Tyr
             20                  25                  30

Asp Tyr Val Ser Trp Tyr Gln His Pro Gly Lys Ala Pro Lys Leu
         35                  40                  45

Met Ile Tyr Asn Val Asn Lys Arg Pro Ser Gly Val Ser Glu Arg Phe
     50                  55                  60

Ser Gly Ser Lys Ser Ala Asn Thr Ala Ser Leu Thr Ile Ser Gly Leu
 65                  70                  75                  80

Gln Asp Asp Asp Glu Ala Asp Tyr Tyr Cys Ser Ser Tyr Ala Arg Arg
                 85                  90                  95

Asp Thr Tyr Ile Phe Gly Gly Gly Thr Arg Leu Thr Val Leu Gly Gln
```

-continued

```
              100                 105                 110
Ala Asn Gly Glu Gly Gly Ser Gly Gly Gly Ser Gly Gly Gly Gly
        115                 120                 125

Ser Glu Val Gln Leu Gln Glu Trp Gly Pro Gly Leu Val Lys Pro Ser
    130                 135                 140

Glu Thr Leu Ser Leu Thr Cys Ala Val Ser Gly Phe Ser Ile Ser Ser
145                 150                 155                 160

Gly Tyr Gly Trp Ser Trp Ile Arg Gln Ser Pro Gly Lys Gly Leu Glu
            165                 170                 175

Trp Ile Gly Asp Ile Ser Tyr Ser Gly Asn Ser Arg Tyr Asn Pro Ser
            180                 185                 190

Leu Lys Ser Arg Val Thr Ile Ser Arg Asp Thr Ser Lys Asn Gln Phe
        195                 200                 205

Ser Leu Lys Leu Thr Ser Val Thr Ala Ala Asp Thr Ala Val Tyr Tyr
    210                 215                 220

Cys Ala Arg His Asp Arg Gly Trp His Glu Tyr Phe Asp Phe Trp Gly
225                 230                 235                 240

Gln Gly Val Leu Val Thr Val Ser Ser
                245
```

ANTIBODY WITH SPECIFICITY FOR COLON CANCER

CROSS-REFERENCE TP RELATED APPLICATIONS

This application is a filing under 35 U.S.C. §371 of International Application No. PCT/Se01/00395, filed on Feb. 23, 2001, which claims benefit of Swedish Application No. 0000597-5, filed on Feb. 24. 2000.

FIELD OF THE INVENTION

The present invention relates to a binding structure which binds in, and/or to the surface of, tumour cells; a target structure displayed and/or expressed in, or to the surface of, tumour cells; a binding structure that recognises and blocks said target structure; a substance that binds to or blocks the expression of said target structure; pharmaceutical compositions comprising said binding structure, target structures or substance as active principles; vaccine compositions comprising said target structures as active principles; a method for phage selection; and methods of in vitro and in vivo diagnosis and prognosis, and of treatment of human malignant diseases comprising the use of the above subject matters.

BACKGROUND OF THE INVENTION

The transformation of normal cells to cancer cells is associated with genotypic and/or phenotypic alterations of both the transformed cells and the microenvironment of the growing tumour (Kerbel R S, 1995). Principally, some of these alterations could be recognised by the immune system as tumour specific antigens (TSAs), and thus form the basis for tumour specific immunotherapy. Although mutation events, underlying tumour priming and tumourigenesis, per se may lead to the expression of TSAs, secondary changes like dysregulated expression and posttranslational modifications of normal antigens may include the majority of tumour associated antigens useful as targets for immunotherapy.

Molecules associated with the tumour phenotype can be identified using modern technologies of genomics and proteomics that directly involve the targets themselves for identification of molecular modifications and altered expression levels (Williams K L, 1999). More indirectly, tumour associated antigens (TAAS) characterising the tumour phenotype have also been identified using hybridoma derived monoclonal antibodies (Kohler G. Milstein C, 1976).

The phage display technology has become an established alternative to the hybridoma technology and for some applications even the method of choice for the generation of monoclonal antibodies by an antigen driven selection principle rather than by pure screening (Hoogenboom H R et al, 1998). The technology is based upon bacteriophage particles that on their surface display the particular antibody fragment encoded in their genome allowing the selection of the phage and its encoding DNA as a genetic package. Provided that primers complementary to antibody variable heavy and light chain genes are available, the antibody genes to be inserted in phage vectors can be amplified by polymerase chain reaction (PCR) from immune or non-immune animals of any species, and large phage antibody libraries constructed.

The selection of phage libraries on cells, tissue sections and other biological materials have generated monoclonal antibodies or peptides binding to components within the complex antigen materials used (Hoogenboom H R et al 1998, Tordsson J et al 1997). The outcome from straight positive selections using complex antigens represents an assortment of specificities from the total tissue reacting repertoire, biased towards highly expressed and immunodominant antigens and to high affinity interactions. To rather identify differentially expressed antigens, representative of the specific phenotype, subtractive approaches have to be employed.

BRIEF SUMMARY OF THE INVENTION

According to the present invention a binding structure, such as an antibody, binding to tumour cells, especially epithelial tumour cells, such as colorectal, pancreatic, breast and lung carcinoma cells, is provided. There is also provided target structures displayed and/or expressed in, and/or on the surface, of such tumour cells.

There is also provided a new subtractive selection method using tissue sections or combinations of tissue sections and cells as the materials for phage selection.

Thus, in one of its aspects, the present invention relates to a binding structure which binds in, and/or to the cell surface of, tumour cells, which binding structure is predominantly determined by the heavy chain CDR structures defined essentially by the amino acids number 160-165 (CDR1), 180-195 (CDR2), 228-238 (CDR3) of the amino acid sequence shown in SEQ ID NO: 2, while additional binding specificity is provided by one or more of the light chain CDR structures defined essentially by the amino acids number 23-36 (CDR1), 52-58 (CDR2), 91-100 (CDR3) of the amino acid sequence shown in SEQ ID NO: 2.

In a further aspect, the present invention relates to a binding structure which binds in, and/or to the cell surface of, tumour cells, said binding structure comprising one or more of the complementarity-determining region (CDR) sequences of an antibody, in the light chain comprising essentially the amino acids number 23-36 (CDR1), 52-58 (CDR2), 91-100 (CDR3) of the amino acid sequence shown in SEQUENCE LISTING ID NO: 2, and the CDR sequences in the heavy chain comprising essentially the amino acids number 160-165 (CDR1), 180-195 (CDR2), 228-238 (CDR3) of the amino acid sequence shown in SEQUENCE LISTING ID NO: 2.

In one embodiment, said binding structure comprises all of said CDR sequences.

In a further embodiment, said binding structure is an antibody and/or fragments thereof, which in further embodiments comprises the variable region of a light chain comprising essentially the amino acids number 1-110 of the amino acid sequence shown in SEQUENCE LISTING ID NO: 2, and the variable region of a heavy chain comprising essentially the amino acids number 130-249 of the amino acid sequence shown in SEQUENCE LISTING ID NO: 2. In yet another embodiment, said antibody comprises the whole amino acid sequence shown in SEQUENCE LISTING ID NO: 2.

In one embodiment, said binding structure binds strongly and/or homogeneously in, and/or to the cell surface of, epithelial tumour cells chosen from the group comprising primary and/or metastatic colorectal, pancreatic, breast and lung carcinoma cells. In a further embodiment, said binding structure binds weakly and/or heterogeneously and/or not to renal and/or prostatic carcinoma and/or malignant melanoma cells. In another embodiment, said binding structure binds strongly to apical parts of the colonic surface epithelium and the epithelium of the small bowel. In a further embodiment, said binding structure binds to the apical aspect of the cell surface of microvilli and/or brush border of the colonic superficial epithelial cells. In a still further embodiment, said binding structure binds weakly to moderately to the mammary glandular epithelium and/or its surrounding connective tissue.

In further embodiments, said binding structure binds weakly and/or heterogeneously and/or not to normal tissues comprising spleen, kidney, liver, lung, skin, pancreas, thyroid, cardiac muscle, and/or the CNS.

In one embodiment, said binding structure is provided by phage selection, phage selection in a further embodiment comprises a combination of an in vivo immunologically preselected repertoire of binding structures displayed on phage particles and a subtractive selection of phage particles by use of pairs of tissues of different phenotypes. In a further embodiment, said sequences are of *Macaca fascicularis* origin, which sequences may have an amino acid identity of at least 78% (Vl) and 86% (Vh) to corresponding sequences of human origin.

In a still further embodiment, said binding structure has low immunogenicity or non-immunogenicity in humans.

In one embodiment, said binding structure has been derivatised by genetically linking to polypeptides, and/or by chemical conjugation to organic or non-organic chemical molecules, and/or by di-, oligo- or multimerisation.

In further embodiments, said binding structure is genetically linked or chemically conjugated to cytotoxic polypeptides or to cytotoxic organic or non-organic chemical molecules; or to biologically active molecules; or to immune activating molecules.

In further embodiments, said binding structure has been changed to increase or decrease the avidity and/or affinity thereof; or to increase the production yield thereof; or to influence the pharmacokinetic properties thereof; or to impart new pharmacokinetic properties thereto.

In a still further embodiment, said binding structure is labelled, and the binding thereof is specific and inhibitable by an unlabeled form of said binding structure and not by other binding structures, and it is not inhibiting the binding of other binding structures having other specificities.

In another aspect, the present invention relates to a DNA sequence coding for the antibody as defined above, that is the antibody comprising the amino acid sequence shown in SEQUENCE LISTING ID NO: 2, which DNA sequence comprises the sequence shown in SEQUENCE LISTING ID NO: 1.

In another aspect, the present invention relates to a target structure displayed and/or expressed in, or on the surface of, tumour cells, said target structure having the ability of being specifically bound by and to specifically bind to a binding structure as defined above, and to other binding structures with similar binding properties.

In one embodiment, said target structure has the ability of being specifically blocked by and to specifically block said binding structures.

In further embodiments, said target structure is displayed and/or expressed strongly and/or homogeneously in, and/or on the cell surface of, epithelial tumour cells chosen from the group comprising primary and/or metastatic colorectal, pancreatic, breast and lung carcinoma cells.

In still further embodiments, said target structure is displayed and/or expressed weakly and/or heterogeneously and/or not in renal and/or prostatic carcinomas and/or malignant melanoma.

In further embodiments, said target structure is displayed and/or expressed strongly in apical parts of the colonic surface epithelium and the epithelium of the small bowel.

In still further embodiments, said target structure is displayed and/or expressed in association with the apical aspect of the cell surface of microvilli and/or brush border of the colonic superficial epithelial cells.

I further embodiments, said target structure is displayed and/or expressed weakly to moderately in the mammary glandular epithelium and/or its surrounding connective tissue.

In still further embodiments, said target structure is displayed and/or expressed weakly and/or heterogeneously and/or not in normal tissues comprising spleen, kidney, liver, lung, skin, pancreas, thyroid, cardiac muscle, and/or the CNS.

In another embodiment, the display and/or expression of said target structure is associated with epithelial tissue.

In a further embodiment, said target structure has an apparent molecular weight in its non-reduced form of 90 and/or 220 kilodaltons.

In a further aspect, the invention relates to an anti-idiotype of a target structure as defined above, which anti-idiotype is specifically bound by and specifically binds to a binding structure having similar binding specificity for said target structure.

In one embodiment, said anti-idiotype is specifically blocked by and specifically blocks said binding structures.

In a still further aspect, the present invention relates to a binding structure which recognises a target structure as defined above and which is of an organic chemical nature. In one embodiment, this binding structure blocks the binding of the binding structure as defined above.

In yet another aspect, the present invention relates to a substance which blocks the expression of a target structure as defined above.

In one embodiment, said substance is an anti-sense oligonucleotide and/or ribozyme molecule.

In a further aspect, the present invention relates to a substance which blocks the function of a target structure as defined above.

In a still further aspect, the present invention relates to a pharmaceutical composition comprising as an active principle at least one binding structure as defined above.

In a further aspect, the present invention relates to a pharmaceutical composition comprising as an active principle a target structure as defined above, or an anti-idiotype of said target structure as above.

In a still further aspect, the present invention relates to a pharmaceutical composition comprising as an active principle a substance as defined above.

In a further aspect, the present invention relates to a vaccine composition comprising as an active principle a target structure as defined above, or an anti-idiotype of said target structure as defined above.

In a still further aspect, the present invention relates to a method for phage selection comprising a combination of an in vivo immunologically preselected repertoire of binding structures displayed on phage particles and subtractive selection of phage particles by use of pairs of tissues of different phenotypes.

In one embodiment of said method, said preselected repertoire of binding structures are antibodies originating from a primate.

In a further embodiment of said method, said pairs of tissues are matched. Preferably, said matched pairs of tissues originate from the same individual.

In further embodiments, said tissues are used in form of frozen and/or formalin-fixed/paraffin embedded tissue sections and/or fragments and/or cell suspensions.

In a further aspect, the present invention relates to a method of in vitro histopathological diagnosis and prognosis of human malignant disease, wherein a sample is contacted with at least one of the binding structures, as defined above, and an indicator. Preferably, said sample is a tissue sample which has been frozen and/or formalin-fixed and paraffin embedded before sectioning.

In some embodiments, said method comprises tumour typing, tumour screening, tumour diagnosis and prognosis, the monitoring of premalignant conditions.

In a still further aspect, the present invention relates to a method for in vitro diagnosis and prognosis of human malignant disease, wherein concentrations in bodily fluids of at least one binding structure as defined above is assayed.

In yet another aspect, the present invention relates to a method for in vitro diagnosis and prognosis of human malignant disease, wherein concentrations in bodily fluids of an antigen comprising a target structure, as defined above, or an anti-idiotype of said target structure, as defined above, is assayed.

In a still further aspect, the present invention relates to a method for in vitro diagnosis and prognosis of human malignant disease, wherein concentrations in bodily fluids of a complex of a) an antigen comprising a target structure, as defined above, or an anti-idiotype of said target structure, as defined above, and b) at least one binding structure, as defined above, is assayed.

In yet another aspect, the present invention relates to a method for in vivo diagnosis and prognosis of human malignant disease, wherein the localisation of at least one binding structure, as defined above, to tumour deposits in a human subject is determined. In one embodiment, said binding structure is administered to the subject before the determination. In a further embodiment, said binding structure is accumulated in tumour deposits. In a still further embodiment, said method is quantitative.

In a further aspect, the present invention relates to a method for therapy of human malignant disease, wherein at least one binding structure, as defined above, is administered to a human subject.

In further embodiments of said method, said binding structure has been changed by being genetically linked to molecules giving the combined molecule changed pharmacokinetic properties, or by being derivatised.

In yet another aspect, the present invention relates to a method for therapy of human malignant disease, wherein a target structure, as defined above, is administered to a human subject. In one embodiment of said method, an immune response to said target structure is elicited.

In further embodiments, said target structure has been changed by being genetically and/or chemically linked to molecules giving the combined molecule changed pharmacokinetic properties, or by being genetically and/or chemically linked to molecules giving the combined molecule changed immunogenicity and/or antigenicity properties, or by being derivatised, or by being genetically modified. In further embodiments of said method, said target structure has been mixed with other molecules to give the mixture changed immunogenicity properties, or with adjuvants.

In a further aspect, the present invention relates to a method for therapy of human malignant disease wherein a substance as defined above is administered to a human subject. In further embodiments of said method, said substance has been changed by being genetically and/or chemically linked to molecules giving the combined molecule changed pharmacokinetic properties, or by being derivatised. In one embodiment, an immune response to said substance is elicited. In further embodiments of said method, said substance has been changed by being genetically and/or chemically linked to molecules giving the combined moleculechanged immunogenicity and/or antigenicity properties; or by being genetically modified. In still further embodiments, said substance has been mixed with other molecules to give the mixture changed immunogenicity properties, or mixed with adjuvants.

DETAILED DESCRIPTION OF THE INVENTION

In the selection method according to the invention tissue sections or combinations of tissue sections and cells are used as the materials for phage selection. Mildly fixed tissue sections should represent biological material with the original structure and phenotype highly preserved.

The method was developed and applied using an immune colon cancer phage library for subtractive selection on matched autologous pairs of colon and colon cancer tissues resected from six different patients. One of the selected specificities, here named K293, reacted homogeneously with all of the tumours used in the selection but very restrictedly to normal colon. Clones with the K293 specificity pattern were frequently found in the last selection rounds suggesting functionality of the tissue based subtraction approach.

Preferential expression of the K293 defined tumour associated antigens (TAA) by the tumour phenotypes developed in patients rather than by in vitro cultured tumour cell lines underlines the advantage and relevance of using tissue sections as the selection materials when aiming for identification of reagents to novel and therapeutically appropriate tumour associated antigens.

Furthermore, the K293 antibody demonstrated strong reactivity with colorectal, pancreatic, lung and breast carcinoma and highly restricted reactivity when tested on a large panel of normal tissues. Cell surface reactivity was demonstrated and together with lack of demonstrable levels of antigen in circulation, suitability of this antigen for tumour targeting was suggested. This was also supported by K293 Fab-superantigen SEA (D227A) demonstrating preliminary evidence of targeted therapeutic activity in a humanised SCID model using heterotransplanted human tumour cells.

Finally, by affinity chromatography using immobilised K293 antibody fragments, purification of a protein fraction could be accomplished. The fraction appeared as a MW 35-45 kDa band by non-reducing SDS gel chromatography, and peptidic digestion and sequencing yielded three peptide fragment sequences supporting homology to GAPDH, glyceraldehyde-3-phosphate dehydrogenase.

The present study suggests a strategy to identify phenotypic differences between normal and diseased tissues, and indirectly the genes encoding differently expressed molecules. This strategy was applied on identifying colon cancer associated antigens and antibodies reacting with these antigens. In a wider perspective, the developed method may likewise be applied in other research fields using tissue pairs such as normal versus inflamed or mature versus immature tissues for identification of inflammatory disease or developmental status markers and targets.

The efficacy of using tissue sections as the antigen source for subtraction of phage libraries was evaluated in a model system. A clear subtraction of one binding phage antibody from another could be achieved using phage encoding scFv antibodies representing broadly-reactive (C215) and tumour-specific (1F) specificities. The latter is a slight simplification since the 1F antigen is weakly expressed but not completely absent on small bowel tissue (Tordsson et.al submitted). Consequently, a minor subtraction also of the 1F phage may have reduced the separation of the two specific phage.

In addition, when acetone fixed tissue sections of Colo 205 tumours grown in SCID mice are used instead of cultured intact Colo 205 cells for the positive selection step (and uterus tissue sections for negative selection step) the yield of 1F phage decreased 12 to 16-fold more than did the C215 phage yield (FIG. 2 and data not shown). An interpretation could be that the 1F antigen is sensitive to fixation or that binding of the 1F scFv phage is sensitive to the harsh washes used in the tissue-based selection method.

The addition of a negative selection step using uterus sections did not change the relative yield of the C215 and IF phage from cells as compared to positive selection only (Tordsson et.al submitted) confirming the specificity of the system and the negative reaction with uterus previously found by immunohistochemistry using these specificities.

In conclusion, in spite of the lack of an optimal tumour-specific phage in the model, efficiency and specificity in the tissue-based phage adsorption was demonstrated, thus providing a basis for a subtractive discovery protocol. In addition, repeating the adsorption step within each selection round (with a minimum loss of phage yield) or between selection rounds will increase the efficiency of adsorption.

Since the library selections were performed before it was demonstrated that repeated negative adsorption steps in each subtractive selection round was more efficient, only single adsorptions were used in all seven selection rounds. This may not have been a drawback. It could be expected that different strengths of the negative selection achieved by performing various numbers of adsorptions in each selection round would act like a tuner. By this, one could gradually bias the selection outcome from antibodies to highly (broadly) expressed antigens (no negative adsorption) towards antibodies to strictly differentially expressed antigens (repeated negative selection).

However, the present data from model experiments demonstrate that the power of positive selection greatly exceeds that of negative selection. Also, some of the specificities were found at low frequencies in a narrow window of one to two selection rounds, after which continued rounds of selection seemed to saturate the selection filter and the composition of specificities changed towards more broadly reactive antibodies.

An observation made during the subtractive library selection was the many selection rounds needed to obtain a high percentage of binding phage. This should be compared to the 2-3 rounds normally sufficient when selecting positively on cells or tissue sections. This indicates that the selection served as an efficient filter for the majority of the specificities in the library and may provide a basis for designing optimal selection strategies. E.g., a smaller enrichment factor allows a larger number of tumours to be used before the optimal selection round is reached. This would bias selection towards the identification of commonly expressed tumour-restricted antigens.

The majority of monoclonal antibodies to tumour associated antigens are murine antibodies generated by the hybridoma technology. However, antibody responses that discriminate between minor variations of normal human antigens, such as alloantigens, have more often successfully been elicited in humans and near-human species.

Only frequent TAAs are practically useful targets for immunotherapy in a large patient population. This excludes unique individual-tumour specific mutations although these represent truly tumour specific antigens. Since frequently expressed tumour-associated antigens in the majority of cases represent normal or minimally altered (e.g. posttranslationally modified) antigens, primates immunised with human tumours may be a superior source of antibodies to such tumour associated antigens.

By the combination of such repertoires with subtractive phage selection, further dissection of the repertoire may be feasible and the outcome of specificities could be better controlled. The identification of a completely different set of anti-tumour antibodies from the immune colon cancer library when using the subtractive tissue based selection according to the present invention as compared to direct positive selection (Tordsson et al submitted) supports this hypothesis.

The selected clones represented by the K293 specificity demonstrated highly homogenous staining of all colorectal carcinoma tissues included in the selection protocol, and very limited reactivity with normal colonic epithelia. The subtractive selection filter defined a narrow phenotype specificity for allowing passage, found in the small difference between normal and malignant colonic epithelia which was common in six individuals, i.e. the patients from which each such matched pair of tissue originated. It was clear from the specificity analysis that the criteria set up for the filter was almost completely fulfilled by the K293 type of specificity.

Eukaryotic cells have previously been used for subtractive selections to identify cell surface antigens. However, in contrast to when using cells for phage selection, tissue sections would permit the identification of reagents to all tissue components expressed in vivo, including antigens regulated by tissue environmental factors or structures that are impossible or difficult to reproduce in vitro.

Two of the four tested colorectal cancer cell lines expressed no detectable K293 antigen either as in vitro cultured cells or when grown in vivo in SCID mice. In addition, another five cell lines cultured in vitro were negative for antigen expression (not shown).

The frequent and homogeneous expression seen for the K293 antigen in patient derived tumours seems to be lost to a large extent when colon cancer cells are cultured in vitro. In addition, the expression could not be induced by growing the cells in vivo in a xenogenic host.

K293FabSEA/E11 fusion protein was the format for extended K293 specificity analysis allowing increased sensitivity and decreased background. This construct was shown to react with a high number of colon, breast and lung carcinomas. In the majority of these tumours K293FabSEA/E11 is positive on 90% or more of the malignant cells. The reaction is not confined to primary tumours since a high frequency of colon cancer metastases also shows strong reactivity. On the other hand, no reaction was obtained in prostate or renal cell cancer and only restricted reaction was seen in malignant melanoma.

Normal tissue reactivity has only been found in the apical part of colon and small intestinal epithelium and in glandular epithelium and its surrounding stroma in normal breast.

Electron microscopy clearly reveals that K293FabSEA/E11 binds to an antigen that is expressed on the cell surface of both normal and malignant cells. In normal colon mucosa the reaction is located at the apical cell surface outlining the microvilli of the superficial epithelial cells. Apical staining also dominates in highly differentiated tumours while low-moderate tumours tend to be homogeneously positive on all aspects of the cell surface.

Although K293FabSEA/E11 does react with mucin-like material in neoplastic glandular formations the antigen could not be detected in a pool of plasma from colon cancer patients. This pool showed high levels of the CA242 colon cancer antigen indicating a high tumour burden in the patients. Since K293FabSEA/E11 is strongly positive on 12 out of 12 examined primary tumours and on 3/4 colon cancer metastases, this indicates that the epitope is not highly expressed on circulating antigen.

The K293FabSEA/E11 shows several characteristics which makes it interesting as a candidate for tumour targeting: 1) it recognises a high frequency of positive primary tumours and metastases, 2) it demonstrated restricted normal tissue reactivity, 3) it binds to an antigen that is expressed on the surface of tumour cells, and 4) it binds to an antigen that is not detectable in the peripheral blood of cancer patients.

The potential use of K293FabSEA/E11 for tumour targeting was further supported by a therapy experiment using humanised tumour bearing SCID mice. Compared to a non-targeted control FabSEA fusion protein, K293FabSEA/E11 showed a more than 80% reduction of LS174T tumours growing in the peritoneal cavity. Immunohistochemical examination of untreated LS174T tumours growing in SCID mice indicates that only 50% of the malignant cells are positive with K293FabSEA/E11 (data not shown). This indicates that some of the K293Fab negative tumour cells potentially could be killed by a bystander effect, possibly by cytokine release from T lymphocytes. Thus, in tumours resected from colorectal cancer patients, demonstrating a higher percentage of positive cells, the therapeutic efficacy should potentially increase.

The K293 antigen might fit into the group of "sequestered" antigens always present in normal tissue but under normal circumstances not exposed to the immune system. In colon and small intestine the antigen is not present on the basal surface of the cells where it would be exposed to circulating antibodies and immunocompetent cells. However, in many tumour samples, the K293 antigen was found distributed over the entire cell membrane and would thus be exposed to the circulation.

K293FabSEA/E11 seems distinct from the specificity profile of existing frequently used colon cancer binding antibodies. It is thus unlikely that it binds to these known target molecules. The apical staining of normal colon by K293FabSEA/E11 show similarities to the reaction seen with anti-CEA. However, antibodies against CEA have also been reported to react with granulocytes and/or macrophages. Furthermore, the CEA antigen is readily detected in the circulation and used as a serum-marker for colo-rectal cancer. The colon cancer reactive antibodies B3, 19-9 and B72.3 all have restricted heterogeneous reactivity in normal colon and also appear distinct from the specificity of K293. This is also true for the MUC-1, -2, -3, -4 antigens which have a different distribution in normal colon as compared to the antigen recognised by K293.

The developed subtractive tissue-based phage selection method according to the invention should add a new dimension to target discovery technologies. Genomics and proteomics are based on the identification of differentially expressed genes and proteins. These methods directly involve the display of the targets themselves whereas the technology of the present invention uses a library of phage displayed reagents to dissect among cell and tissue expressed targets.

The identification of a reagent to a novel target provides efficient means to analyse the tissue distribution of an epitope and for purification and characterisation of its corresponding antigen(s). The demonstration of the successful affinity purification and characterisation by sequence analysis of a putative target antigen for the K293 antibody, exemplifies the strong potential for such antibody probes for efficient and rapid target identification. Three 10 amino acids long peptides show identity to the glyceraldehyde-3-phosphate dehydrohydrogenase molecule, suggesting that it might be a target for K293.

Although genomics may lead to the identification of target genes, this technology fails to secure alterations in posttranslational modifications added at the protein level. Useful information of the genetic expression in various tissues may be supplied by searching gene expression databases (electronic Northern blots), while direct demonstration would require the use of in situ hybridisation.

Proteomics can be used for detection of some types of posttranslational modifications. However, the analysis of the tissue distribution of an identified protein would require either the generation of DNA probes based on its amino acid sequence to be used for in situ hybridisation or the generation of antibody reagents towards the protein.

Neither genomics nor proteomics cover e.g. carbohydrates and lipids and other biological molecules of non-protein nature. A powerful automated technology has been demonstrated which combines proteomics with the phage display technology, or more specifically this means the selection of antibody phage towards protein spots on two-dimensional gels (presented by the company CaT, Cambridge, U.K.). This will undoubtedly generate reagents to novel antigens, but including the limitations of proteomics and the fact that many epitopes exposed on denatured proteins are not exposed in vivo and many epitopes exposed on folded proteins in vivo will not be detected. Of course, such a technology can also be used in a reversed fashion using a reagent generated by the subtractive phage selection approach, to detect the target protein spot followed by mass spectrometry and sequencing for target identification.

The selected antibodies, particularly the K293 specificities, have several advantageous properties for use as tumour targeting moities. These include tumour reactivity with a highly homogenous binding pattern to a large fraction of the tumours of colorectal carcinoma, and potentially also other common tumour types. Importantly, normal tissue reactivity is highly restricted, and the target antigen is not detectable in the circulation of cancer patients, using standard methodology. Also, a primate antibody, highly homologous to human immunoglobulin sequences, is not expected to induce a strong xeno-antibody response (leading to immune complex formation and elimination) in humans.

The present strategy for phage selection is based on the use of an in vivo preselected repertoire of binding structures (antibodies) from a primate in conjunction with a narrow filter for subtractive selection.

A further contemplated application of the invention is in connection with the use of large non-immune libraries to avoid immunisation bias such as immunodominance and this will challenge the dissecting power of designed selection strategies. These include subtractive selection using authentic in vivo phenotype represented by tissue sections, changing background antigenic environment to promote antigens representing "common denominators" of a phenotype, and specific blocking of frequently identified epitopes (by use of cloned antibodies).

The present work clearly demonstrates that phage selection can be used as a discovery tool for a defined target-oriented strategy, and that the selection design criteria are critical to the successful outcome of this.

The present invention will now be illustrated by the following non limiting examples in conjunction with accompanying figures.

EXAMPLE 1

Efficient Subtractive Model Selection

The principle of subtractive selection of phagemid libraries according to the invention is shown in FIG. 1. Individual phage in a library pool to be subtractively selected (with the aim to identify tumour associated antigens) can ideally be classified according to the specificity pattern of their encoded antibodies, namely 1) broadly tissue reactive, 2) tumour restricted, and 3) non-specific. A phagemid library also has a large fraction of phage that do not display their encoded antibodies. These phage can not be specifically adsorbed in the negative selection step, but can be washed away in the positive selection step prior to phage propagation in bacteria.

The broadly reactive phage C215 scFv reactive with the epithelial cellular adhesion molecule, Ep-CAM, and the more tumour restricted phage specificity, 1F scFv (previously identified from the phage library), were mixed ($2.5 \times 10^7$ C215 and $1.3 \times 10^6$ 1F scFv phage) and used in the model experiment shown in FIG. 2A. These phage specificities were incubated on sections of either C215 expressing tissue, small bowel, or on tissue negative for both antigens, uterus. After tissue section adsorption, specific phage remaining in the supernatant was positively selected using Colo 205 cells.

The relative composition of different antibiotic resistance transducing units (different phage clones) in the non-selected and selected phage pool was analysed using colony titration and the yield of phage illustrated for each of the phage specificities. The data demonstrate that adsorption on sections of small bowel reduced the yield of the broadly reactive C215 phage 33-fold as compared to uterus adsorption.

The corresponding reduction for the other specificity, 1F, was only 1.2-fold. The ratio of the phage (1F/C215) as compared to the original mixture changed 50-fold after selection using small bowel sections (1.8-fold using uterus sections).

In a repeated experiment the phage ratio changed 17-fold when using small bowel sections (1.4-fold for uterus sections). The use of tissue sections for both selection steps demonstrated a reduction of subtraction efficiency. The combined use of sections of small bowel/Colo205 SCID tumour and small bowel/primary colon carcinoma did reduce the C215 specific phage yield 4-fold and 3-fold, respectively, as compared to the corresponding setting using uterus for adsorption. However, by repeating the adsorption step twice the adsorption efficiency increased to 25-fold (data not shown). High numbers of specific phage were used in these experiments, $3.8 \times 10^9$ and $1.2 \times 10^{10}$ C215 and 1F phage with a background of $6.1 \times 10^{10}$ non-specific D1.3 phage, demonstrating high adsorption capacity of the small bowel tissue sections in the experiment shown in FIG. 2.B, equally high numbers of phage, $7.2 \times 10^9$ C215, $2.2 \times 10^{10}$ 1F and $4.2 \times 10^{10}$ D1.3 phage were used for two repeated negative tissue adsorptions using uterus, small bowel or lung sections followed by positive selection using Colo205 tumour sections. Small bowel and lung tissue section adsorption significantly ($p<0.05$, $n=4$) reduced C215 phage enrichment (C215/D1.3 phage yield) by a factor of 11 and 2.2-fold respectively as compared to uterus adsorption (FIG. 2B). In contrast, the 1F phage enrichment (55-64 times over D1.3 phage) was not affected by the choice of tissue for adsorption (reduced by a factor of 1.1 and 0.9-fold for small bowel and uterus, respectively).

In conclusion, the negative tissue section adsorption of C215 phage was Ep-CAM tissue antigen dependent and demonstrated up to a 33-fold efficiency. The data also shows that subtractive selection was dependent on the efficiency of both the negative and positive selection step.

Materials and Methods

Animals

*Macaca fascicularis* monkeys were kept at the Swedish Institute for Infectious Disease Control, Stockholm. The monkeys were immunised subcutaneously with a crude suspension of human colorectal tumours with or without alum adjuvant (two individuals each). Booster doses were given day 21, 35 and 49.

Severe Combined Immunodeficient (SCID) female mice (C.B-17) were obtained from Bommice, Ry, Denmark. The mice were kept under pathogen-free conditions in Macrolone cages (III) with sterile pelleted rodent diet from Special Diets Services, Essex, UK and sterile water available ad libitum. Mice (two mice per cell line) aged 8-12 weeks, were injected subcutaneously in each flank with $2 \times 10^6$ colon cancer cells, Colo205, WiDr, HT29 or LS174T, suspended in 200 µl 1% Balb/c serum. The tumours were grown to a size of 4-5 mm in diameter and then resected and frozen for immunohistochemistry.

All animals were kept according to Swedish legislation and the experiments were approved by the local committee.

Cells and Tissues

The human colorectal cell lines, Colo201 Colo205, Colo320DM, SW480, SW620, WiDr, HT29 and LS174T were from American Type Tissue Culture Collection, Rockville, Md. and Colo137 from CanAg AB, Gothenburg, Sweden. Cells were cultured in RPMI 1640 medium (Gibco) supplemented with 10% heat inactivated foetal bovine serum (FBS) from Gibco and 0.1 mg/ml gentamycin sulphate (Biological Industries, Kibbutz Beit Haemek, Israel). Human tumour and normal tissues were obtained from Lund University Hospital and Malmö General Hospital, Sweden. For subtractive library selections, pairs of primary colorectal carcinoma and normal colonic epithelia tissue (located at a distance of at least 5 cm from the tumour lesion) obtained from six individuals, were used.

Library and Model Phage

The phagemid vector, used for the library and model phage, the primers for amplification and scFv gene assembly by polymerase chain reaction (PCR) of the lambda light chain and heavy chain genes to be inserted into the phagemid vector have been described previously (Tordsson et al., (1997) and Tordsson et.al. (submitted). Briefly, cDNA was amplified from total spleen RNA using an RNA isolation kit from Promega and an RNA PCR kit from PE Biosystems, Stockholm, Sweden. The D1.3, C215 and 1F scFv model phage used in the study encode ampicillin, chloramphenicol and tetracycline antibiotic resistance genes, respectively, to allow analysis of individual phage titers in phage mixtures by colony titration using agar plates containing different antibiotics. The displayed antibodies are reactive with hen egg lysozyme (D1.3), anti-epithelial adhesion molecule (C215) and a hitherto unknown epithelial tumour cell surface molecule (1F, Tordsson et al submitted).

Subtractive Selections

Sections of negative selection tissue (colon, small bowel or uterus) were air-dried on slides, fixed in ice cold acetone and rehydrated in 20% FBS in TBS. Library phage, $10^{10}$ or $10^{11}$ in 20% FBS, or model phage clone mixtures, "mini-libraries" were incubated with the sections for 15-24 h at 4° C. in a humid atmosphere to adsorb non-wanted phage specificities.

The adsorbed phage solution was transferred and incubated as above for positive selection on sections of colon cancer tumours. The sections were washed six times for ten min in TBS buffer and then two times for 5 min in Genenase buffer, 1M NaCl, 10 mM Tris-HCl, 6 mM $CaCl_2$, 1 mM EDTA, pH 8.0. Phage were eluted for 30 min with 400 µl 33 µg/ml Genenase in Genenase buffer at room temperature.

Eluted phage were rescued using 1 ml 10× concentrated *E. coli* strain DH5aF' O.D.$_{600}$ 1.0. Infected bacteria were diluted in 2×YT supplemented with ampicillin at 0.1 mg/ml or chloramphenicol (50 μg/ml), and cultured for 1-24 h at 24-37° C. (until an O.D.$_{600}$ of 0.5 was reached).

Helper phage M13K07 (MOI approx. 10) was added, incubation continued for 2 h after which kanamycin to a final concentration of 70 μg/ml was added and the culture rocked, at 250 rpm and 28° C., until an=O.D.$_{600}$ of 2-3 was reached (1-2 days). The bacteria were pelleted by centrifugation and the phage in the supernatant pelleted by two PEG/NaCl precipitations and centrifugations. The phage pellet was diluted in TBS.

For tetracyclin and chloramphenicol model phage, a 45 min. incubation at 37° C. preceded colony titrations. For chloramphenicol resistant library phagemid constructs, this resistance expression period was extended to 2 h.

Alternatively to tissue sections, live cells in 1% BSA in PBS were used for the positive selection in the model experiments. Adsorbed phage were transferred and incubated on 3 million Colo 205 cells for 1 h. The cells were washed three times for 10 min and then eluted with 100 μl Genenase as described above. In the experiments above a phage with reduced infective capacity and encoded antibiotic resistance gene ($10^{12}$/ml) was added to reduce potential non-specific binding sites.

In model experiments using tissue sections for both the negative and positive selection steps, the non-specific phage D1.3 scFv was used in the same concentration range as the specific phage.

EXAMPLE 2

A Late Enrichment of Library Specificities is Seen and Optimal Diversity is Found in the Second Last Selection Round Although small, the yield of library phage as compared to the internal control phage D1.3 scFv increased between the sixth and seventh selection round indicating enrichment of tissue specific phage in the library.

Figure 3:
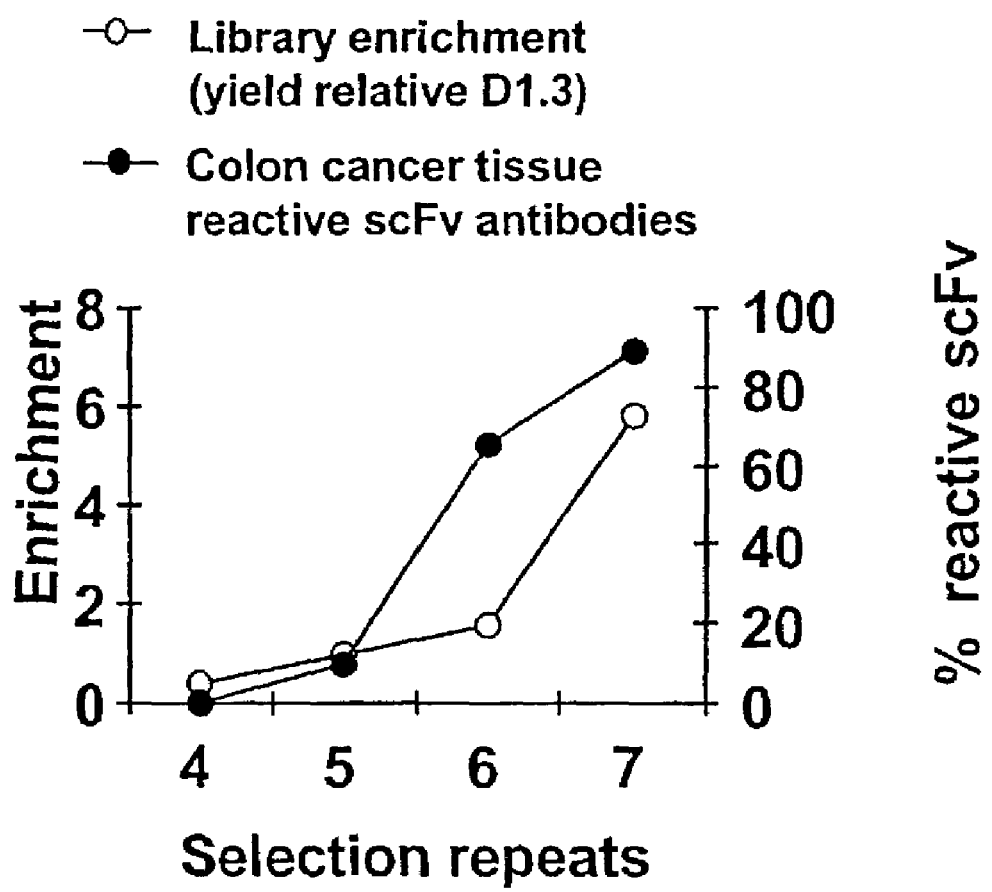

ScFv antibodies were produced by culturing bacterial clones infected with library phage from the last four selection rounds (260-280 clones/selection round). The frequency of scFv antibodies binding to tissue sections of colon cancer and colon, and the relative yield of library phage over the internal control phage (library enrichment) are shown in FIG. 3. Tissue reactive scFv antibodies (29/280) could not be demonstrated until the fifth selection round, suggesting that negative adsorption suppressed enrichment of common broadly reactive specificities.

In previous studies using the same library for positive selection on colon cancer cells (Tordsson et.al. submitted), using a melanoma library for positive selection on melanoma tissue sections (Tordsson et al., 1997) and positive selections on various tumour cells (unpublished results), a high frequency of specific phage was achieved already in the second or third selection round.

Figure 4:
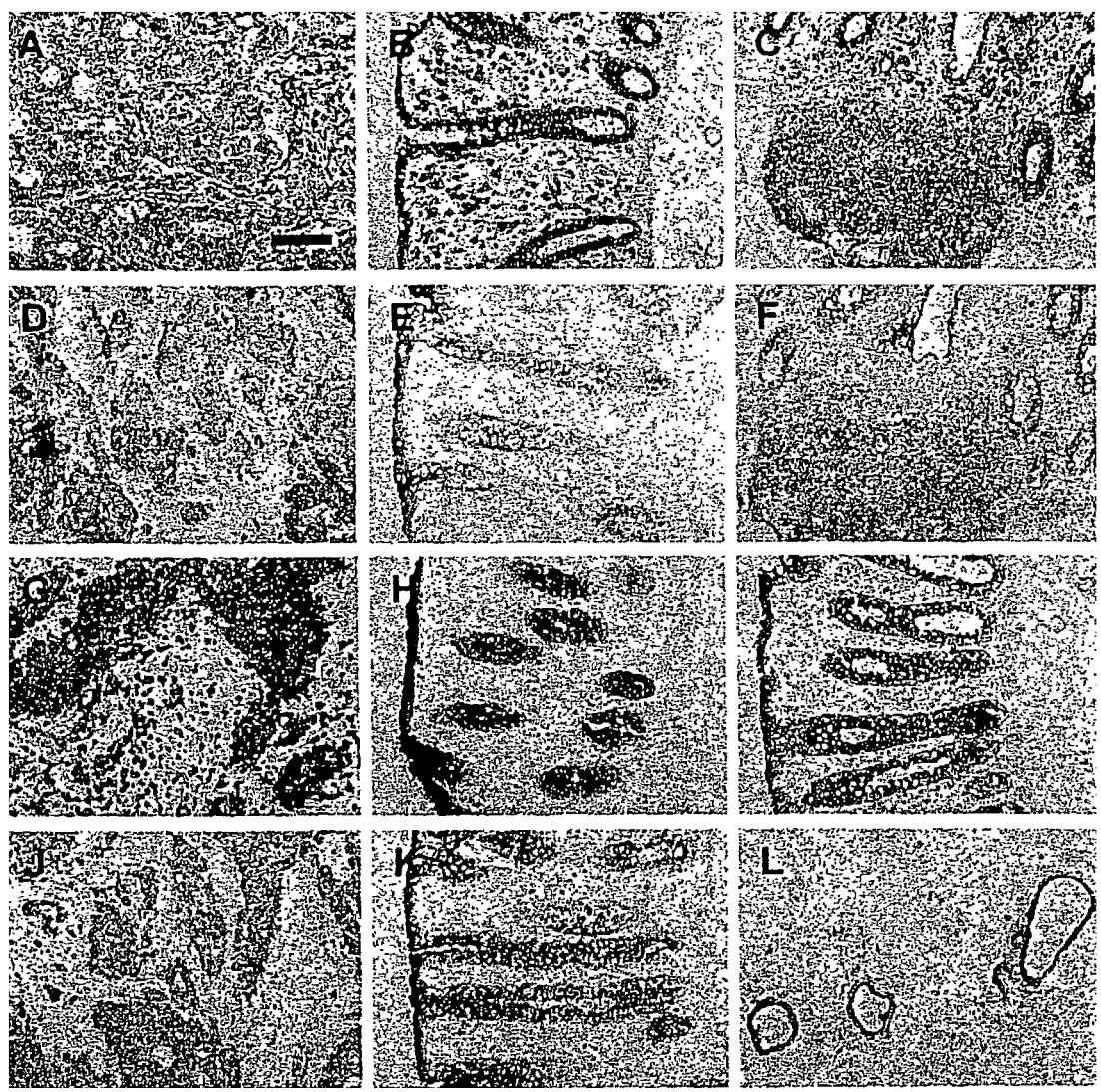

In addition, novel specificities not previously selected from the colon cancer library have now been identified using the developed method for subtractive tissue section selection. Immunohistochemical staining patterns of scFv antibody clones representing the six identified specificity groups, are shown in FIG. 4. The antibody K302 scFv strongly reacts with colon cancer tissue (A) but also broadly with epithelial, lamina propria and Peyer's patch cells in the colon (B, C). The K293 scFv reacts with cells and deposited material (possibly mucins) in tumour tissue (D), and only with the luminal side of normal colon epithelia and not with the Peyer's patch (E, F). The K320 scFv antibody reacted with tumour cells and putative infiltrating cells within the colon cancer tissue (G). This antibody strongly reacted with normal colon epithelia deeply into the crypts, but not with cells in the lamina propria (H). The K294 scFv reacted with a pattern that suggests intracellular location of the recognised antigen in colon (I) and colon cancer (not shown). The clone IIID9 scFv reacted with colon cancer cells but not with deposited material or infiltrating cells (J). It reacted deeper into the colon crypts than K293 scFv but seemed more restricted than K320 scFv (K). The last antibody specificity, IID11scFv, stained the surface layer lining the inside of blood vessels (most likely endothelial cells, L).

The composition of the specificity patterns changed over the last three selection rounds (Table 1). Only two patterns were found in the fifth selection round, the most tumour-restricted group K293, and the more broadly reactive K302 group. The high frequency of the K293 group decreased and the K302 group increased after the last round, whereas their frequencies did not change significantly between the fifth and sixth selection round. Four additional specificity patterns appeared in the sixth selection round. Three of these patterns disappeared in the last round.

In conclusion, the second last selection round demonstrated optimal diversity of specificity groups with a high number of specific versus non-specific phage in the library, whereas the broadly reactive K302 specificity group dominated after the last selection round. This demonstrates the importance of screening the optimal selection round to find a broad variety of specificities and suggests that the negative selection filter was efficient up to the sixth selection round, after which it was saturated.

TABLE 1

| | Frequency (%) of binding scFv Specificity per selection round (R) | | |
|---|---|---|---|
| Specificy groups: | R5 | R6 | R7 |
| K293 | 69 | 65 | 28 |
| K302 | 31 | 31 | 71 |
| K320 | 0 | 1.1 | 0 |
| K294 | 0 | 1.1 | 1.7 |
| IIID9 | 0 | 0.6 | 0 |
| IID11 | 0 | 0.6 | 0 |
| Total frequency of binders: | 10 | 65 | 89 |

EXAMPLE 3

A Frequent and Homogeneous Tumour Selective Antigen Expression is Demonstrated by a K293-superantigen Fusion Protein A representative, K293, of the most tumour restricted specificity group was recloned to be genetically linked to an immunological effector molecule, a D227A mutant of the superantigen Staphylococcal Enterotoxin A, SEA (D227A). This fusion protein was fermentor cultured and purified, and used to demonstrate homogeneous reactivity with five of the tumours used. Reactivity of the fusion protein K293 scFv-SEA(D227A) demonstrates equally homogeneous staining of the colon cancer tumour shown in FIG. 5 as compared to the Ep-CAM specific fusion protein C215 Fab-SEA(D227A). The staining of deposited material inside tumour ducts and the restricted colon reactivity to surface epithelia was confirmed using the K293 scFv-SEA(D227A) fusion protein.

Materials and Methods

ScFv Antibody and scFv-SEA(D227A) Production

Individual clones of *E. coli* non-supressor strain HB2151, transduced with phage from the sixth and seventh library selection rounds, were cultured in microwell plates (Nunc) in 2×YT medium supplemented with 100 µg/ml ampicillin for 17 h at 37° C. Aliquotes were transferred to microwell plates with low phosphate medium and antibiotics for expression of scFvs from the phoA promoter, and cultured at 30° C. for 17 h. The cells were pelleted by centrifugation at 2200 rpm for 7 min. and supernatants transferred to plates containing an equal volume/well of 1% bovine serum albumine (BSA) in PBS. ScFv-SEA(D227A) fusion proteins were produced by fermentation and purified using a rabbit anti-SEA coupled affinity column, according to Tordsson et al., (1997) and standard methods. The purified fusion proteins were quantified in a sandwich type ELISA using anti-SEA and biotinylated anti-SEA antibodies as capture and detector antibodies. The integrity of the fusion proteins was confirmed by immunoblot analysis using biotinylated rabbit-anti-SEA antibodies.

Immunohistochemistry

Sections (6-8 µm) were fixed in ice cold acetone and rehydrated in 20% FBS in 150 mM NaCl, 50 mM Tris pH 7.6 (TBS). Endogenous biotin was blocked with avidin and biotin (Vector Laboratories, Burlinngame, Calif.). Primary scFvs (culture supernatants) or scFv-SEA(D227A) fusion proteins, 5 µg/ml, were incubated with the sections for 1 h. A rabbit antiserum to the C-terminal tag, ATPAKSE, followed by biotinylated goat anti-rabbit antibodies (DAKO A/S), 1 µg/ml, was used to detect the scFvs. The fusion proteins were detected using affinity purified and biotinylated rabbit anti-SEA antibodies, 5 µg/ml.

These reagents and the following, StreptABComplex HRP (DAKO A/S) diluted 1/110 in 50 mM Tris pH 7.6, were incubated for 30 min. Between all steps the sections were washed 3 times in TBS. The staining reaction was developed for 8 min in 0.5 mg/ml 3,3'-diaminobenzidine tetrahydrochloride (Sigma) dissolved in Tris pH 7.6 with 0.01 percent $H_2O_2$. After 10 min counterstaining in 0.5% methyl green, the slides were rinsed for 10 min in tap water and gradually dehydrated in 70-99% ethanol and xylene before mounting in DPX medium (Sigma).

Finger Printing scFvs

ScFv genes (representatives of scFv specificities) were amplified by polymerase chain reaction. Aliquots, 5 µl, of microwell bacterial cultures and primers complementary to regions 5' and 3' of the scFv gene in the phagemid vector of the transfected bacteria (regions in the phoA promoter and in the M13 gene III) were used. Hinf I restriction patterns of the amplified scFv genes were analysed by running a 1% agarose gel electrophoresis. Clones with unique patterns or prototype patterns were chosen and stored as representatives of each immunohistochemical specificity group.

EXAMPLE 4

Absence or Down-regulation of K293 Antigen Expression in vitro Reflects the Advantages of a Tissue Based (Representing Preservation of an Authentic in vivo Phenotype) Selection Principle Mildly fixed frozen tissue sections of tumours resected from patients (as compared to cultured tumour cells) is a source of complex antigens (for phage selection) that closely resembles the original tumour phenotype. In contrast to the homogeneous and frequent reactivity with patient derived tumours, the K293 scFv-SEA(D227A) antibody reacted weakly with 2/9 (HT29 and LS174T) and did not react with 7/9 (Colo201, Colo205, Colo137, Colo320DM, SW480, SW620, and WiDr) colon cancer cell lines by flow cytometry, in contrast to moderate to strong reaction with C215 Fab-SEA (D227A) (Table 2, and results not shown). Two of the negative cell lines (Colo2O5 and WiDr) and the two weakly reactive cell lines were grown sub cutaneously in SCID mice.

Immunohistochemistry was used to analyse the reactivity of K293 scFv-SEA(D227A) with these tumours. The Colo205 tumour was completely negative whereas tumour cells of the WiDr tumour was negative but deposited material was positive. The HT29 tumour was positive for a minor fraction of the cells, approximately 5-10%, and for deposited material. The LS174T tumour was heterogeneously positive for approximately 50% of the cells and positive for deposited material. Thus, the frequent and homogeneous expression of the K293 epitope in primary patient tumours is neither observed in in vitro cultured tumour cell lines nor in tumours derived from cell lines grown in a xenogenic host. This demonstrates that the use of tissue sections as the antigen source for phage selection was essential to find the tumour restricted K293 specificity.

Figure 6:
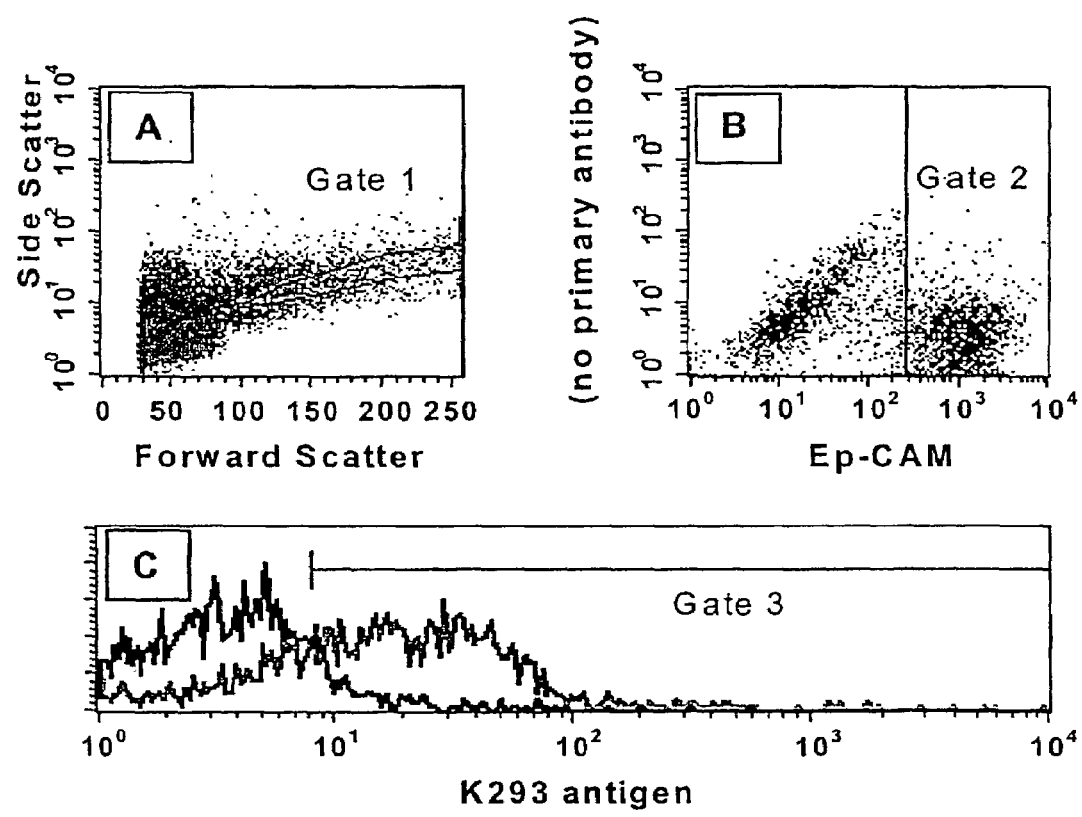

The weak expression of the K293 epitope on two cell lines detected by flow cytometry suggests that the recognized TAA can be expressed on the surface of the tumour cells. Surface expression in vivo was confirmed by flow cytometry performed on tumour cells derived from resected primary colon carcinomas and treated with Dispase (a neutral protease) and collagenase to disintegrate the tumours into cell suspensions. The tumour cells, distinguished from other cells (such as fibroblasts, blood cells and smooth muscle cells) as Ep-CAM+ cells as detected with mAb C215, were double stained for K293scFv-SEA(D227A) reactivity (FIG. 6). A large fraction of the Ep-CAM positive tumour cells were K293 reactive (approximately 60%) after the o.n. enzymatic treatment required to extract the cells.

Although with variable strength, K293scFv-SEA(D227A) reactivity could-be demonstrated in three additional experiments using cells from resected primary tumours, supporting that the K293 TAA is expressed on the surface of tumour cells in the autologous host. Table 2. The K293 antibody homogeneously stains primary colon carcinomas but only weakly and heterogeneously colon cancer cell lines cultured in vitro or in xenogenic host, i.e. subcutaneously in SCID mice.

| Cell line | Flow cytometry | S.c growth in SCID mice | Primary colon carcinomas |
|---|---|---|---|
| Colo205 | Negative | Negative | Homogeneous staining of five primary colon carcinomas used for selection* |
| WiDr | Negative | Negative* | |
| HT29 | Weakly positive | 5-10% positive cells* | |
| LS174T | Weakly positive | 50% heterogeneously positive* | |

*Deposited material is strongly positive.

Materials and Methods

Flow Cytometry

Reactivity of antibodies genetically linked to Staphylococcal Enterotoxin A, SEA, to cultured or freshly prepared tumour cells, was demonstrated using biotinylated rabbit anti-SEA antibodies and avidin-PE.

Primary human colon cancer cells were derived from colorectal cancer tumours resected the same day and kept on ice in 150 mM NaCl until use (less than 4 h). The tumours were cut into small pieces and slowly rocked in a solution containing 1 mg/ml collagenase (Sigma), 0.1 mg/ml hualuronidase (Sigma), 2.4 mg/ml Dispase (Boehringer Mannheim) and 20 µg/ml deoxyribonuclease (Sigma) diluted in RPMI 1640 medium (Gibco, Middlesex, UK) at room temperature over the night. The tumour cells were separated from tissue debris by filtration, washed once with PBS/1% BSA and then stained with 5 µg/ml C215 mAb/rabbit-anti-mouse-FITC (Dakopatts) diluted 1/20 and with 5 µg/ml K293scFv-SEA (D227A)/biotinylated polyclonal rabbit anti-SEA antibodies diluted 1/1000/avidin-PE diluted 1/20.

EXAMPLE 5

K293FabSEA/E11 Strongly and Frequently Stain Epithelial Tumours

Figure 7:
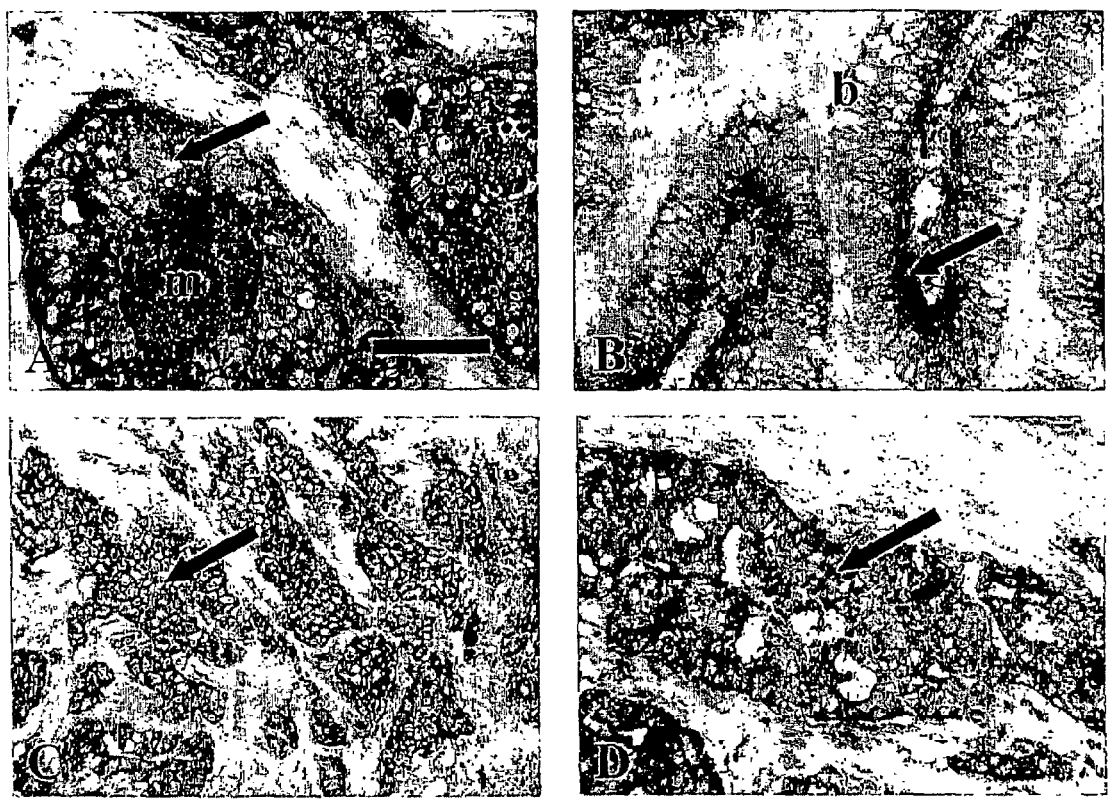

The immunohistochemical reaction on various human tumours are summarised in table 3. K293FabSEA/E11 show strong positive reaction in adenocarcinomas from colon, pancreas, lung and breast (FIG. 7). Strong reaction are found both in malignant cells and in mucin-like/shed material in glandular structures. No reaction has been obtained in kidney or prostate cancer while one of two malignant melanomas showed weak to moderate reaction. In colon cancer all 12 examined tumours are strongly positively stained.

The frequency of positive malignant cells within the individual tumours vary from 75 to 100%. Five out of 6 breast tumours were found strongly positive with a frequency of positive malignant of 75-100%. Although the frequency of positive cells within the colon and breast carcinomas vary from 75 to 100%, the majority of tumours shows a more than 90% positive reaction. Two out of 2 examined pancreatic tumours also show strong reaction in more than 90% of the malignant cells.

Among the non small lung carcinomas (NSCLC) 2 are squamous cell carcinoma and 4 are lung adeno carcinomas. All showed strong staining of the malignant cells. In both examined squamous cell carcinomas positive staining were seen in more than 90% of the tumour cells. In the adeno carcinomas 2 showed 90% tumour cell reactivity and 2 were positive on less than 10%.

The reactivity pattern of K293FabSEA/E11 on different colon cancers seems to correlate to the differentiation degree of the tumour. In highly differentiated tumours, apical staining of the malignant cells dominates. In some of these highly differentiated tumours baso-lateral parts of the malignant cells are completely negative while apical parts are strongly positive. In low and moderately differentiated tumours the immunoreaction is not polarised to a certain part but rather uniformly distributed in the malignant cells.

TABLE 3

Tumour tissue reactivity, K293FabSEA/E11

| Colon cancer, primary tumours | Strong staining in 12/12 tumours. 75-100% tumour cell reactivity. Strong reaction is also seen in mucin-like/shed material. |
|---|---|
| Colon cancer, metastasis | Strong staining in 3/4 tumours*. 75-100% tumour cell reactivity. |
| Pancreas cancer | Strong staining in 2/2 tumours. Ca 90% tumour cell reactivity. |
| Breast cancer | Strong reaction in 5/6 (75-100% tumour cell reactivity). Reaction is also seen in mucin-like/shed material. |
| Non small cell lung carcinoma | Strong reaction in 6/6. <10% tumour cell reactivity in 2/6, >90% in 4/6. |

TABLE 3-continued

Tumour tissue reactivity, K293FabSEA/E11

| (NSCLC) | Reaction is also seen in mucin-like/shed material. |
|---|---|
| Malignant melanoma | Weak-moderate reaction in 1/2 (ca 90% tumour cell reactivity). Neg. in 1/2. |
| Prostate cancer | Neg. 2/2. |
| Kidney cancer | Neg. in 2/2. |

*One of the positive metastasis were formalin fixed and paraffin embedded.

EXAMPLE 6

K293FabSEA/E11 Shows a Very Restricted Normal Tissue Crossreactivity

Figure 8:
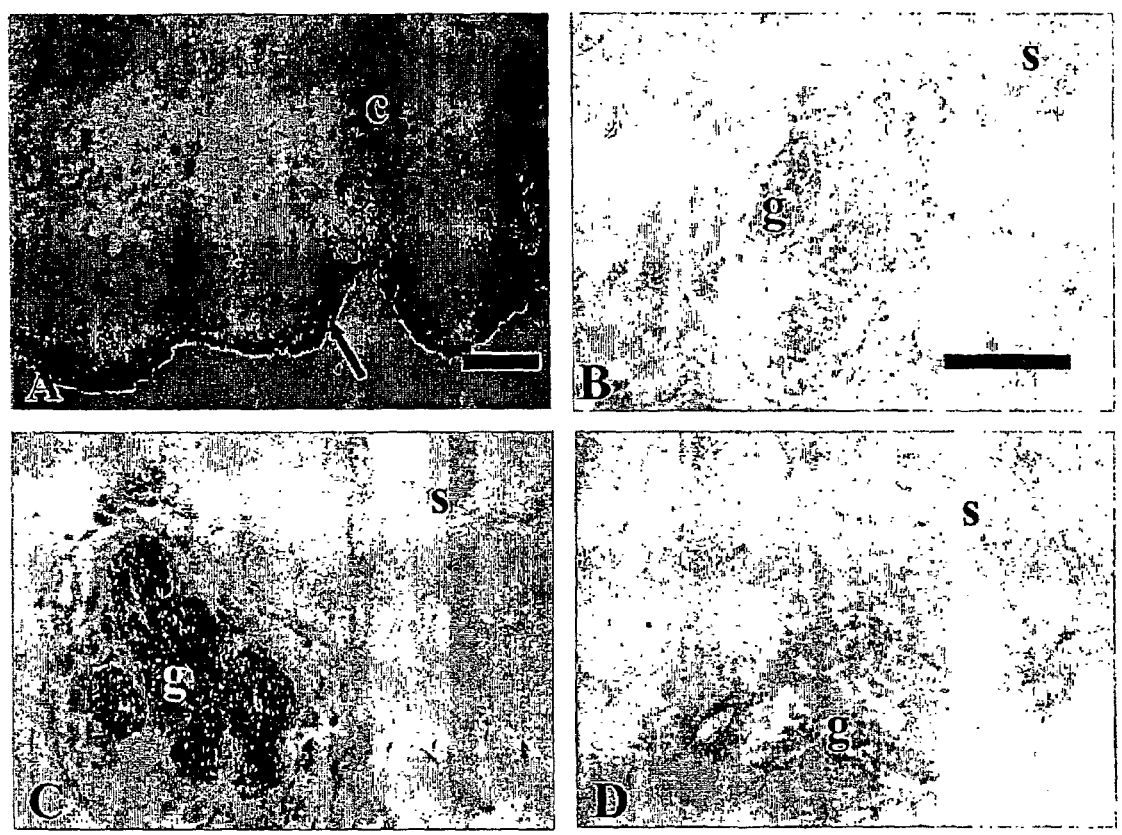

Normal tissue reactivity is, among the panel of studied organs, restricted to colon, small intestine and breast. A strong staining of the apical part of epithelial cells is seen in colon (FIG. 8). This is also found in one of the two examined biopsies from small intestine. Possibly these biopsies are collected from different regions indicating that K293FabSEA/E11 only reacts with certain parts of the small intestine. In breast tissue weak to moderate reaction is seen in glandular epithelial cells and in parts of the surrounding stroma (FIG. 8). No reaction is seen in stomach, spleen, kidney, liver, lung, skin, pancreas, thyroid, cardiac muscle or CNS (table 4).

TABLE 4

Normal tissue reactivity, K293FabSEA/E11

| Colon | Strong reaction in apical parts of the epithelium. 5/5 |
|---|---|
| Small intestine | Strong reaction in epithelium in ½ |
| Stomach | Neg. 2/2 |
| Breast | Weak to moderate reaction in glandular epithelium and surrounding stromal parts. 2/2 |
| Spleen | Neg. 2/2 |
| Kidney | Neg. 2/2 |
| Liver | Neg. 2/2 |
| Lung | Neg. 2/2 |
| Skin | Neg. 2/2 |
| Pancreas | Neg. 2/2 |
| Thyroid | Neg. 1/1 |
| Cardiac muscle | Neg. 1/1 |
| CNS | Neg. 1/1 |

Materials and Methods

Immunohistochemistry

Cryosections for Light Microscopy

Tumour and normal tissues kindly provided by the Department of Surgery, Lund University Hospital were snapfrozen in isopentane that had been precooled in liquid nitrogen and stored at −70° C. After cryosectioning the sections were air dried over night. Sections were fixed in cold acetone, blocked for endogenous biotin with avidin/biotin (Vector, Burlingame Calif.) and then incubated with the primary antibody K293FabSEA/E11 for one hour.

The fusion protein was prepared by genetically fusing the K293 VH and VL genes (obtained from the scFv selected from the library) to cynomolgus CH1 and C-lambda genes. The combined Fab was linked to the superantigen Staphylococcal Enterotoxin AE chimeric mutant (D227A, (demonstrating a strongly reduced MHC Class II binding) E11. This construct, K293FabSEA/E11, demonstrated very low levels of non-specific binding and allowed sensitive detection by secondary antibodies polyclonal rabbit anti-SEA antisera, produced and biotinylated by standard methods.

The secondary antibodies were incubated for 30 min. followed by a streptavidin-biotin/HRP (Dakopatts, Copenhagen) step for another 30 minutes. Between all steps, washes were performed three times with 0.05 M Tris pH 7.6 and 0.15 M NaCl. Diaminobenzidine (DAB) was used as chromogen and the sections were counterstained in 0.5% methyl green. As positive control, a pan-epithelial reactive fusion protein, C215FabSEA(D227A) was used. As negative control a fusion protein between a non tissue reactive Fab and SEA-D227A or no primary antibody was used. All antibodies were used at a concentration of 5 µg/ml. Results are expressed as negative, weak, moderate or strong staining, respectively.

Paraffin Sections for Light Microscopy

Tumour tissue of a lymphatic colon cancer metastasis was fixed in 4% formaldehyde (Sigma, St. Louis Mo.) at 4° C. over night. After rinsing in PBS the tissue was dehydrated and embedded in paraffin (Histolab AB, Gothenburg, Sweden). Paraffin sections were prepared and allowed to dry at 37° C. over night. The sections were deparaffinised, rehydrated and immunohistochemically stained as described above.

EXAMPLE 7

K293FabSEA/E11 Recognises a Surface Expressed Antigen

The sub-cellular localisation of the immunoreaction is more accurately demonstrated on thin sections compared to 8 µm cryo sections. In 2 µm plastic sections it was possible to demonstrate apical as well as baso-lateral cell membrane staining of colon cancer cells (FIG. 9A). This tumour specimen was also processed for electron microscopy. At the resolution of the electron microscopy it was possible to demonstrate that the immunoreaction is located at the outer surface of the malignant cells. Staining followed by microscopy of 2 µm semithin sections and electron microscopy of normal colon also demonstrate that the immunoreaction is located at the level of the outer surface of microvilli in the luminal epithelium (FIGS. 9B and C).

Materials and Methods

Plastic Sections for Light Microscopy and Electron Microscopy

Tumour and normal tissue material were processed according to the following description. Fresh resection material was fixed in a mixture of 4% formaldehyde (Sigma, St. Louis Mo.) and 0.25% glutaraldehyde (TAAB, Berkshire) for 2 hours. After rinsing in PBS the tissues were cryoprotected by rinsing in PBS containing 30% sucrose over night and then snapfrozen in isopentan/liquid nitrogen as above. 50 µm free floating cryosections were incubated with the same antibodies as described for light microscopy but the incubation times differed. The primary antibody was incubated over night, the secondary for 3 h and streptavidin-biotin/HRP for another 3 h. After reaction in DAB the sections were postfixed in 1% $OsO_4$ (Standard supplies, Kåallered) dehydrated and embedded in Epon (Agar Scientific Ltd, Stansted, U.K.).

Semithin sections (2 µm) for light microscopy and ultrathin sections (50-60 nm) for electron microscopy were prepared on an ultramicrotome (LKB, Bromma, Sweden). Semithin sections were counterstained with 1% methylene blue. Ultrathin sections were stained in an ultrastainer (LKB, Bromma) in 2% uranylacetate and leadcitrate.

EXAMPLE 8

Figure 10:
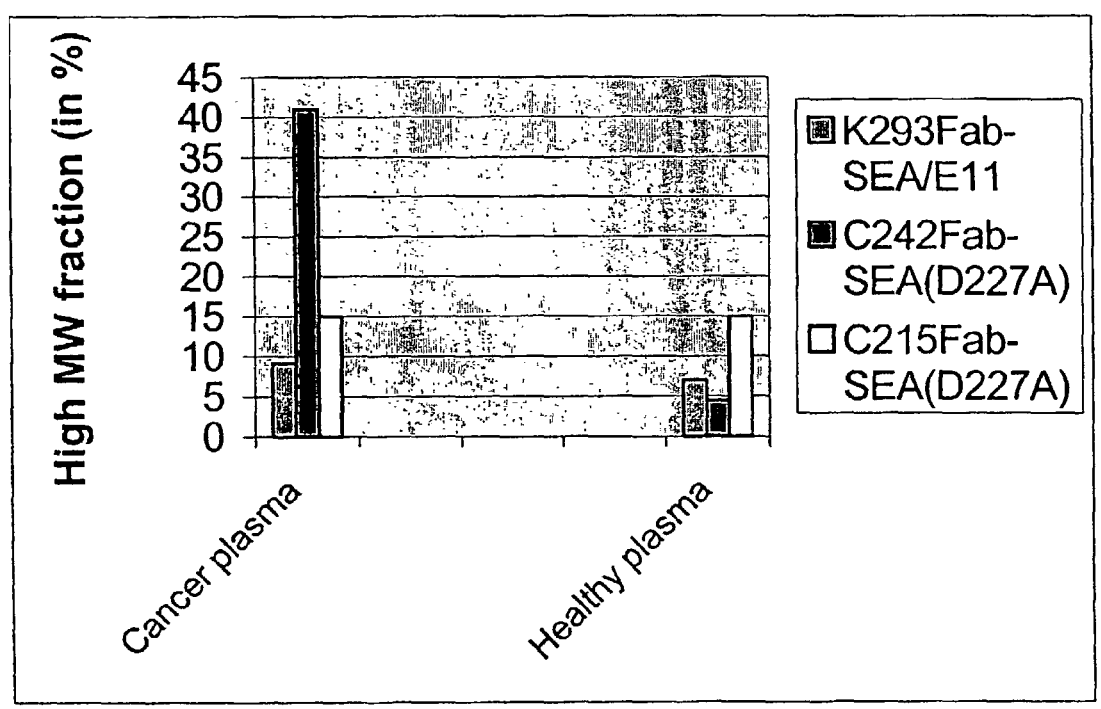

K293FabSEA/E11 Does Not Detect Circulating Antigen In Sera from Colon Cancer Patients FIG. 10 demonstrates the size of the fraction of radiolabelled SEA fusion protein constructs and circulating tumour antigen, after incubation with plasma samples from colorectal cancer patients and one healthy volunteer, respectively.

For the K293Fab-SEA/E11, less than 1.5-fold more was found as protein complexes when incubated with plasma from cancer patients, as compared to incubation with plasma from the healthy individual. On the other hand, for the C242-Fab-construct (positive control) eightfold more was in complex form when incubated with plasma from cancer patients. Thus, the K293Fab-SEA/E11 did not recognise any circulating antigen in cancer patients.

Materials and Methods

Test Compound Formulation

50 µg of K293Fab-SEA/E-11, C215Fab-SEA$_{mut.9}$ and C242Fab-SEA$_{mut.23}$ were labelled with $^{125}$I to a specific activity of 10 µCi/µg using Iodogen precoated tubes (Pharmacia-Amersham Biotech) (Fraker and Speck, 1978). The labelled test compounds were determined with respect to protein concentration and specific radioactivity by HPLC (see below).

Plasma samples were collected from colorectal cancer patients (n=12) demonstrating high levels of circulating CA242 antigen by a commercial assay (CanAG Diagnostics AB, Gothenburg, Sweden) and from one healthy volunteer with a very low level of plasma CA242.

Analysis of Test Solutions in Plasma

50 µl of undiluted plasma samples were incubated with 1 µg/ml of test compound (diluted in PBST) for 60 min at ambient temperature and the incubation mixture shaking. All samples were analysed by HPLC (see below).

Since the plasma samples contained antibodies to SEA and could give a false positive interaction signal, they were incubated with protein A to remove the immunoglobulins. After this removal step the anti-SEA content was <10 pmol/ml. The plasma content of CA242 in the pooled plasma from cancer patients was 479 U/ml and less than 20 U/ml in the healthy donor sample after incubation with protein A.

The labelled test compounds and the prepared samples were analysed by size exclusion HPLC. 50 µl of sample were injected (Waters 717 Auto Sampler) and separated on a TSK G3000 SW column (7.5×600 mm, Toso Haas). The sample was eluted with 10 mM PBS, pH=7.4, at a flow rate of 1.0 ml/min at ambient temperature. Detection was performed with a UV detector (A280 nm, Waters 486) and a radioactivity detector (Flo-One, A-515-AX) coupled in series and the data were collected during 35-60 min depending on the sample. Fractions containing complex bound test compound were observed as high molecular weight peaks appearing earlier in the chromatogram than the test compound it self. Fractions containing iodinated fragment or free iodine were observed as low molecular weight peaks. The radioactivity chromatograms were integrated and the area of the complexed test compounds and of the low molecular weight peaks were expressed in percent of the total area.

EXAMPLE 9

Purification of a Tumour Associated Antigen that is Recognised by the Colon Cancer Reactive Antibody K293

A tumour extract was made out of human colon cancer tissue. The extract was applied to two columns, a control and pre-column coupled with C215Fab-SEAm9 and a column coupled with K293Fab-SEAm9. The columns were connected in series when applying the tissue extract onto the columns but were separated during the alkaline elution of the bound proteins.

Figure 11:
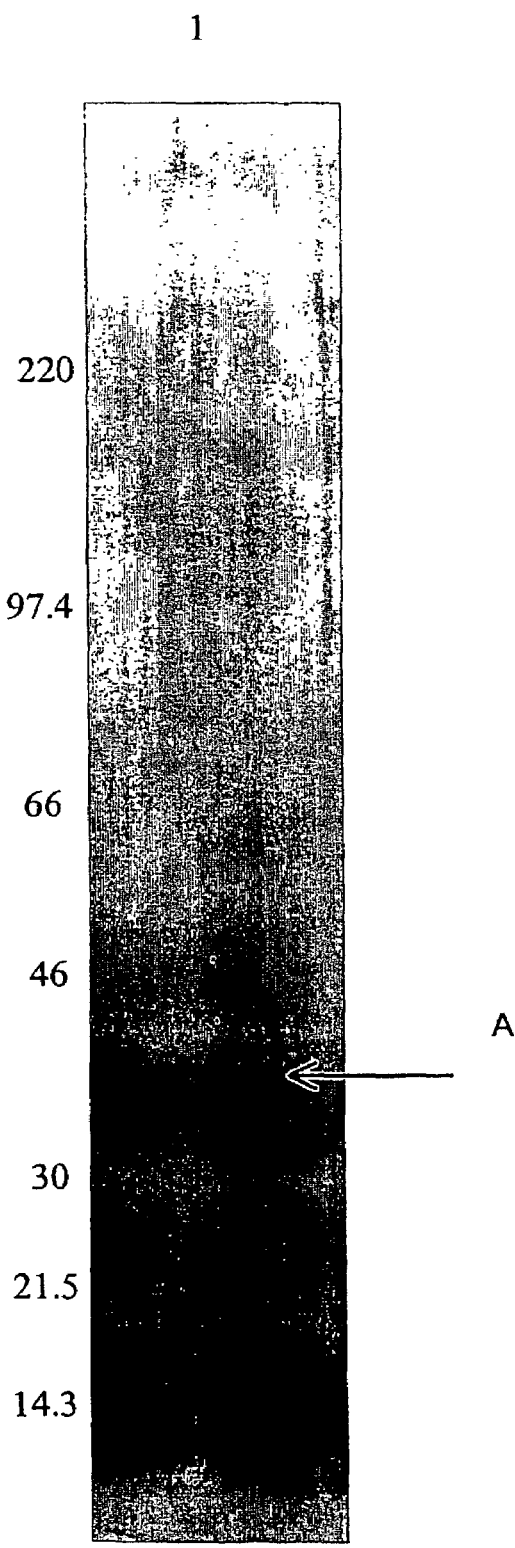

Eluted fractions from the K293Fab-SEAm9 coupled column were collected, neutralised, concentrated and then analysed by SDS-PAGE under non-reducing conditions (FIG. 11). A major band (labelled A in FIG. 11) could be seen at approximately 35-45 kDa in the fraction eluted at high pH. The major band was cut out and proteolytic digestion with trypsin was performed. The generated tryptic peptide fragments were separated and the sequences of the ten first N-terminal amino acid residues were determined for three of these isolated peptides (FIG. 12). The three short N-terminal peptide sequences determined (SEQUENCE LISTING ID NO 3-5) show complete homology to parts of the human protein glyceraldehyde 3-phosphate dehydrogenase (GADPH) (FIG. 13).

Materials and Methods

Solubilisation of Tumour Tissue

Human colon cancer tissue expressing the K293 antigen was provided by hospitals in Sweden and store frozen at −70° C. in the tissue bank of ABR. Frozen colon cancer tissues were sliced with a scalpel and transferred into a tube with 4° C. pre-cooled isotonic sucrose buffer (0.25 M sucrose, 10 mM KCl, 1.5 mM MgCl, 50 mM Tris-HCl pH 7.4 at 25° C.) containing 1% (v/v) Nonidet P-40 (NP-40) and protease inhibitors (Complete™ Protease Inhibitor Cocktail Tablet, Boehringer Mannheim). Tissue slices were homogenised with an Ultra-Turrax homogeniser and were left to solubilise at 0° C. The solubilised solution was centrifuged at 11000 rpm (Hettich centrifuge, Universal 30 RF rotor) to remove most of the cell debris. The supernatant was further centrifuged at 108000×g at 4° C. (Beckman ultracentrifuge, Ti-60 rotor) and finally filtered through a 0.2 μm Minisart plus filter (Sartorius A G, Göttingen, Germany).

Affinity Purification of Tissue Antigens

The antibodies, K293Fab-SEAm9 and C215Fab-SEAm9 were coupled to NHS-activated HiTrap® columns (Pharmacia Biotech, Uppsala, Sweden) according to the manufacturer's instructions. The control and pre-column coupled with C21SFab-SEAm9 and the column coupled with K293Fab-SEAm9 were connected in series and were pre-washed with start buffer (20 mM Tris-HCl, pH 7.5 at 4° C., containing 0.2% NP-40). Then the extract was loaded onto the column at 0.1 ml/min and the flow-through was recirculated and then followed by washing of the columns with the start buffer. The bound antigens on each column was eluted with a gradient of dietylamine from pH 7, which reached pH 11 in 20 min. Fractions of 0.5 ml were collected, neutralised with 0.1 ml of 1 M Tris-HCl, pH 6.7 and stored at −20° C. The purification was performed at 4° C. using an ÄKTA FPLC system from Amersham Pharmacia Biotech (Uppsala, Sweden). The eluted fractions were pooled, concentrated and then analysed on SDS-PAGE. Identified protein bands were cut out and stored at 4° C. The proteins were then digested with trypsin and the N-terminal peptide sequence was determined for individual peptides-at the Protein Analysis Center (Karolinska Institute, Stockholm, Sweden).

EXAMPLE 10

K293FabSEA/E11 are Able to Suppress Tumour Growth in Severe Combined Immunodeficient (SCID) Mice The superantigen SEA has the ability to activate T lymphocytes to cytokine production and cytotoxicity. When a superantigen is fused with a tumour reactive antibody it is targeted to tumour cells. Localisation of the superantigen in the tumour area then leads to selective killing of the tumour cells.

Figure 14:
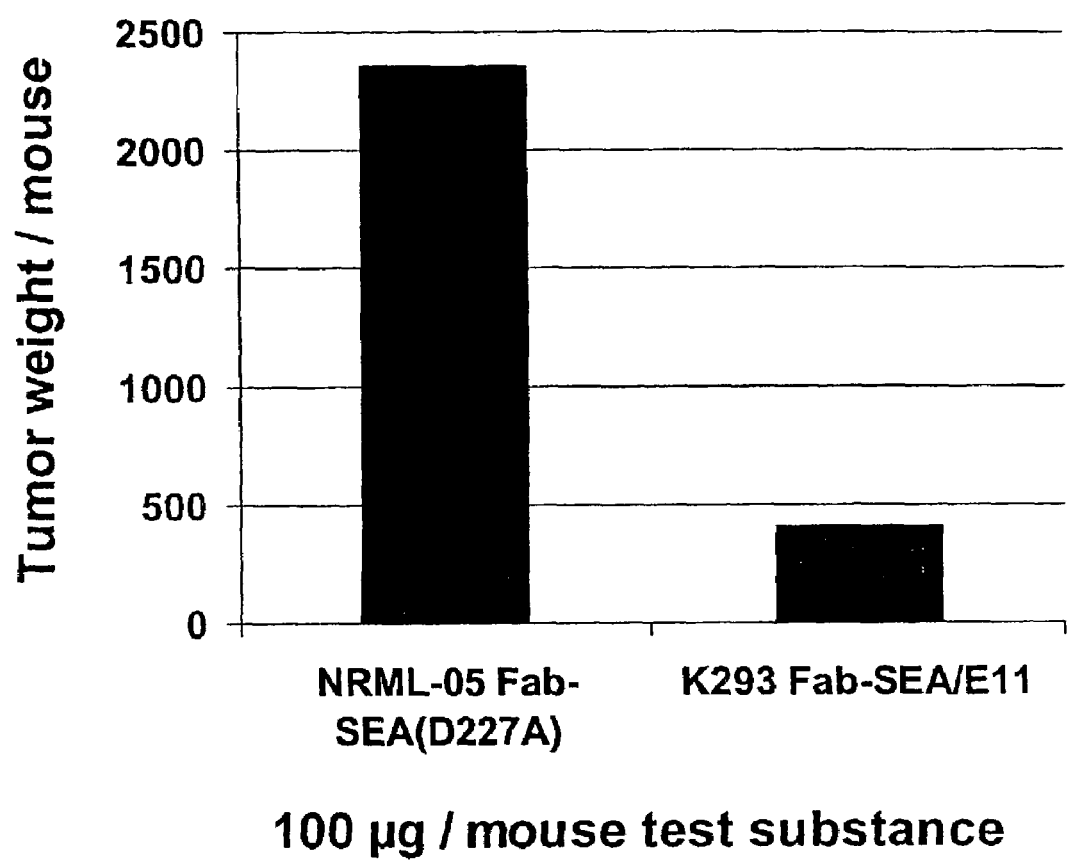

The result of the experiment is presented in FIG. 14 which shows that animals treated with K293FabSEA/E11 have an 80% reduction of tumour mass compared to control animals treated with a non-targeted NRML-05 (anti-melanoma) Fab-SEA (D227A).

Materials and Methods

Severe combined immunodeficient (SCID) mice (Bommice, Ry, Denmark) were injected i.p. with $5\times10^6$ LS174T colon cancer cells (ATCC, Rockville, Md.) in 0.2 ml vehicle (PBS-1% Balb/c serum). 24 h later the mice were injected i.p. with $20\times10^6$ human peripheral-blood mononuclear cells (PBMC) prepared by Ficoll-Hypaque separation of buffy coats obtained from blood donors at the University Hospital of Lund Sweden. On day 1, 3 and 6 after tumour injection the animals were treated with 100 μg of NRML-05FabSEA/D227A (6 animals) or 100 μg K293FabSEA/E11 (7 animals). On day 51 the animals were sacrificed, tumour nodules were removed and the mass was determined.

REFERENCES

Hoogenboom H R, de Bruine A P, Hufton S E, Hoet R M, Arends J W, Roovers R C. Antibody phage display technology and its applications. (1998) Immunotechnology 4:1

Kerbel R S. Significance of tumor-host interactions in cancer growth and metastases. (1995) Cancer Metastasis Rev 14:259

Kohler G, Milstein C. Derivation of specific antibody-producing tissue culture and tumor lines by cell fusion. (1976) Eur J Immunol 6:511

Tordsson J, Abrahmsen L, Kalland T, Ljung C, Ingvar C Brodin T. Efficient selection of scFv antibody phage by adsorption to in situ expressed antigens in tissue sections. (1997) J Immunol Methods 210:11

Tordsson J, Lavasani S, Ohlsson L, Karlström P, Svedberg H, Abrahmsén L and Brodin T. A3—a novel colon and pancreatic cancer reactive antibody from a primate phage library selected using intact tumor cells. Submitted to Int J Cancer.

Williams K L. Genomes and proteomes: towards a multi-dimensional view of biology. (1999) Electrophoresis 20:678

FIGURE LEGENDS

FIG. 1. The principle of subtractive selection. Specific adsorption of broadly reactive phage (black) and reduction of non-displaying and non-specific phage (white) by washings during positive selection. The tumour restricted phage (checked) is then eluted.

FIG. 2. Efficient subtractive selection. Negative adsorption on uterus or small bowel tissue sections followed by positive selection on Colo205 cells (A). Two repeated adsorptions on uterus, small bowel or lung tissue sections and positive selection on Colo205 tumour tissue sections (B).

FIG. 3. Late enrichment of a panel of tissue specific phage from the subtractively selected library.

FIG. 4. Immunohistochemical staining patterns of library selected scFvs. Colon carcinoma (A), colon epithelium (B) and Peyer's patch (C) staining with K302 scFv and with K293 scFv (D-F). Colon carcinoma (G) and colon epithelium (H) staining with K320 scFv and with IIID9 scFv (J, K). Colon epithelium staining with K294 scFv (I) and colon blood vessel staining with IID11scFv (L).

Figure 5:
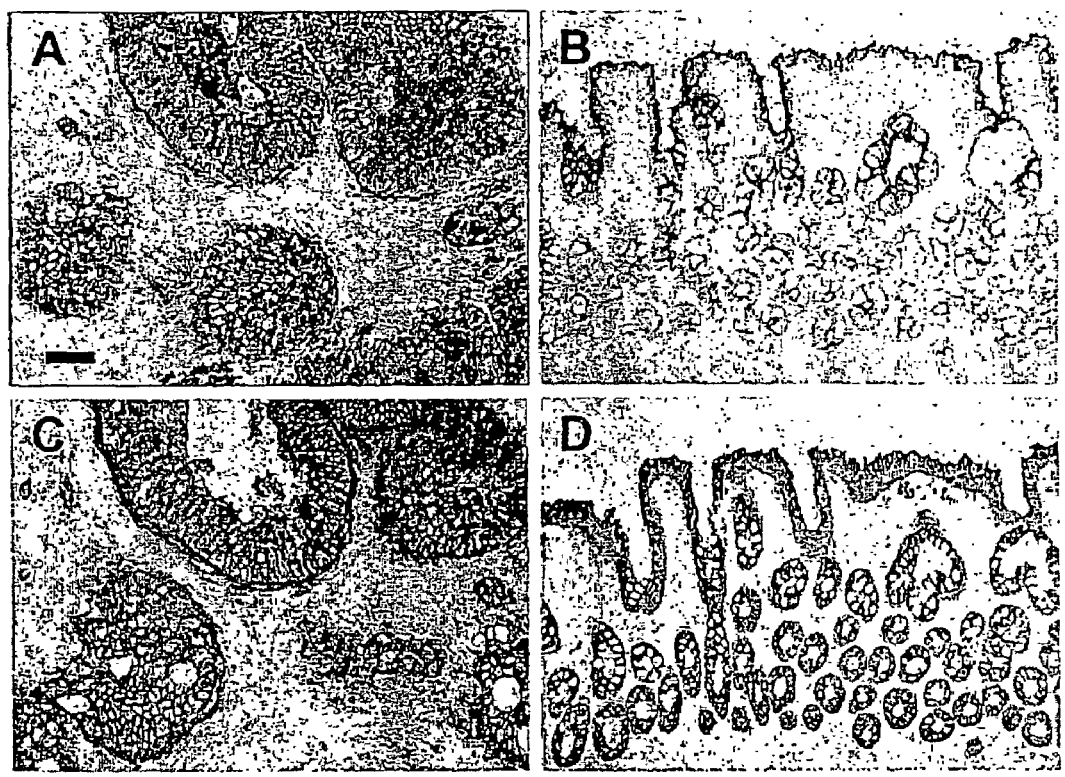

FIG. 5. Immunohistochemical reactivity of K293 scFv-SEA(D227A) to colon cancer (A) and colon (B) and of C215 Fab-SEA(D227A) to colon cancer (C) and colon (D) at 100 nM. The bar in (A) is 100 μm.

FIG. 6. Flow cytometry on colon cancer cells freshly prepared from a resected primary human colon carcinoma. Cells gated for size, granularity (A, B) and Ep-CAM expression as a marker for epithelial cells, were stained with 5 μg/ml K293scFv-SEA(D227A) (gray line) or no primary antibody fusion protein negative control (black line) (C).

FIG. 7. K293FabSEA/E11 staining of different tumours. A. Staining of a moderately differentiated colon cancer showing strong staining of both malignant cells (arrow) and mucin-like material (m) in glandular structures B. Staining of a highly differentiated colon cancer illustrating strong apical staining (arrow) of the malignant cells while basal parts of the neoplastic glandules (b) are unreactive. C. Strong staining of malignant cells in a breast tumour (arrow) D. Strong staining of malignant cells in lung adeno carcinoma (arrow). Bar in A represent 50 μm and is also valid for B-D.

FIG. 8. A. K293FabSEA/E11 staining of normal colon. Note the apical staining of the epithelial cells (arrow). The immunoreaction is found in epithelium facing the lumen of colon, while the crypts (c) are negative. B. K293FabSEA/E11 staining of normal breast. Weak to moderate staining are seen in glandular epithelium (g) and in surrounding stromal parts (s). C. Normal breast stained with a FabSEA fusionprotein between the pan-epithelial marker C215 and SEAD (227A) (FabC215SEA-D227A). Note the strong labelling of the glandular epithelial cells (g). No reaction is seen in stromal parts (s). D. Normal breast negative control (no primary antibody) illustrating no reaction in glandular epithelial cells (g) and in stromal parts (s). Bar in A represent 50 μm. Bar in B 50 μm and is also valid for C and D.

Figure 9:
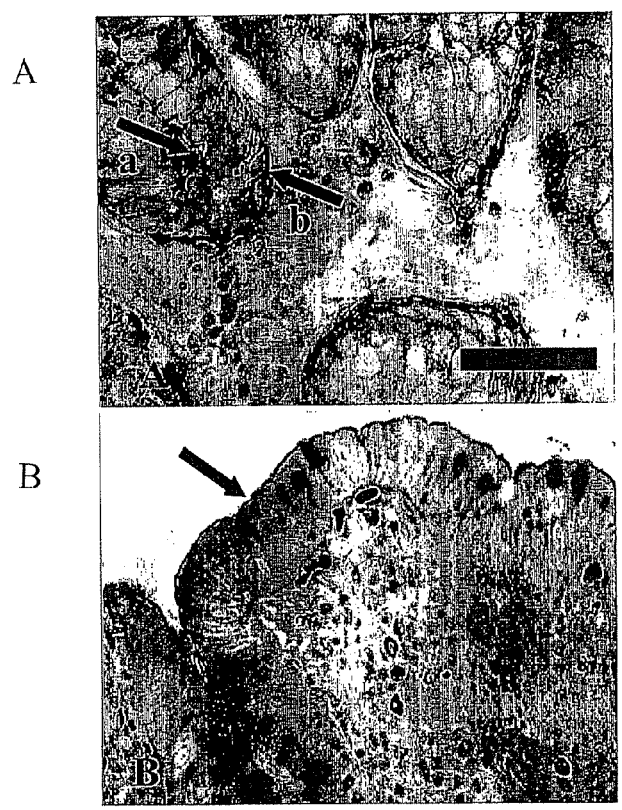
Figure 9:

FIG. 9. Semithin section from colon cancer (A) and normal colon (B) stained with K293FabSEA/E11. In the colon cancer section both basal (arrow b), apical (arrow a) and lateral parts of tumour cells are positively stained. In normal colon positive staining are seen in the apical surface of epithelial cells (arrow). Electron microscopy shows that the immunoreaction is located at the surface of microvilli in normal colon epithelial cells (C, arrow). Bar in A represents 30 μm and is also valid for B.

FIG. 10. Analysis of complex formation of antibody SEA fusion proteins to components of plasma from colon cancer patients and from healthy individuals. The percentage of radioactivity eluted in the high-molecular weight area is plotted. Note the high binding of C242FabSEA to plasma from colon cancer patients.

FIG. 11. Non-reduced SDS-PAGE analysis of the eluted fraction from the K293-coupled affinity column (in lane 1). The major band marked A was cut out for amino acid sequence analysis. The positions of the molecular weight standard used are indicated.

FIG. 12. The N-terminal sequences with SEQUENCE LISTING ID NOS: 3-5 of three tryptic peptide fragments from the 35-45 kDa protein band (labelled A) isolated from K293-affinity purification (see FIG. 1).

FIG. 13. The peptide sequences of SEQUENCE LISTING ID NO 2: 1, 2, and 3 were aligned with the protein sequence of glyceraldehyde 3-phosphate dehydrogenase (Swiss prot. Data base accession no. P04406).

FIG. 14. Immunotherapeutic effect of FabSEA fusion proteins on the growth of LS-174T tumour cells in SCID mice supplemented with human peripheral blood mononuclear cells (PBMC). Note the tumour weight (in mg) reduction after treatment with K293FabSEA/E11.

The invention claimed is:

1. An isolated antibody or antigen binding fragment thereof which binds to tumor cells, wherein said antibody or antigen binding fragment comprises heavy chain CDR sequences comprising amino acids 160-165 (CDR1), 180-195 (CDR2), and 228-238 (CDR3) of the amino acid sequence shown in SEQ ID NO:2, and light chain CDR sequences comprising amino acids 23-36 (CDR1), 52-58 (CDR2), and 91-100 (CDR3) of the amino acid sequence shown in SEQ ID NO:2.

2. The isolated antibody or antigen binding fragment thereof according to claim 1, comprising the variable region of a light chain consisting of amino acids 1-110 of the amino acid sequence shown in SEQ ID NO:2, and the variable region of a heavy chain consisting of amino acids 130-249 of the amino acid sequence shown in SEQ ID NO: 2.

3. The isolated antibody or antigen binding fragment thereof according to claim 2, wherein said antibody or antigen binding fragment thereof comprises the amino acid sequence shown in SEQ ID NO: 2.

4. The isolated antibody or antigen binding fragment thereof according to claim 1, wherein said antibody or antigen binding fragment thereof binds to epithelial tumor cells selected from the group consisting of primary or metastatic colorectal, pancreatic, breast and lung carcinoma cells.

5. The isolated antibody or antigen binding fragment thereof according to claim 1, wherein said antibody or antigen binding fragment thereof does not bind to renal or prostatic carcinoma or malignant melanoma cells.

6. The isolated antibody or antigen binding fragment thereof according to claim 1, wherein said antibody or antigen binding fragment thereof binds to apical parts of the colonic surface epithelium and the epithelium of the small bowel.

7. The isolated antibody or antigen binding fragment thereof according to claim 6, wherein said antibody or antigen binding fragment thereof binds to the apical aspect of the cell surface of microvilli or brush border of the colonic superficial epithelial cells.

8. The isolated antibody or antigen binding fragment thereof according to claim 1, wherein said antibody or antigen binding fragment thereof binds to the mammary glandular epithelium.

9. The isolated antibody or antigen binding fragment thereof according to claim 1, wherein said antibody or antigen binding fragment thereof is provided by phage selection.

10. The isolated antibody or antigen binding fragment thereof according to claim 9, wherein said phage selection comprises the combined use of an in vivo immunologically preselected repertoire of antibodies and/or antigen binding fragments, displayed on phage particles, and a subtractive selection of phage particles by use of pairs of tissues of different phenotypes.

11. The isolated antibody or antigen binding fragment thereof according to claim 1, wherein the CDR sequences of claim 1 are of Macaca fascicularis origin.

12. The isolated antibody or antigen binding fragment thereof according to claim 1, wherein said antibody or antigen binding fragment thereof is non-immunogenic in humans.

13. A pharmaceutical composition comprising as an active principle an antibody or antigen binding fragment thereof according to claim 1.

* * * * *